(12) United States Patent
Davies et al.

(10) Patent No.: US 8,969,327 B2
(45) Date of Patent: Mar. 3, 2015

(54) SUBSTITUTED ANDROST-4-ENE DIONES

(75) Inventors: Huw Davies, Duluth, GA (US);
Dabashis Ghosh, Syracuse, NY (US);
Daniel Morton, Dereham (GB)

(73) Assignees: Emory University, Atlanta, GA (US);
The Research Foundation of State of New York, Syracuse, NY (US);
Hauptman-Woodward Medical Research Institute, Buffalo, NY (US)

(*) Notice: Subject to any disclaimer, the term of this patent is extended or adjusted under 35 U.S.C. 154(b) by 18 days.

(21) Appl. No.: 13/635,924

(22) PCT Filed: Apr. 7, 2011

(86) PCT No.: PCT/US2011/031501
§ 371 (c)(1),
(2), (4) Date: Sep. 19, 2012

(87) PCT Pub. No.: WO2011/127232
PCT Pub. Date: Oct. 13, 2011

(65) Prior Publication Data
US 2013/0157988 A1 Jun. 20, 2013

Related U.S. Application Data

(60) Provisional application No. 61/322,062, filed on Apr. 8, 2010.

(51) Int. Cl.
| | | |
|---|---|---|
| *C07J 75/00* | (2006.01) |
| *A61K 31/5685* | (2006.01) |
| *C07J 1/00* | (2006.01) |
| *C07J 41/00* | (2006.01) |
| *A61K 45/06* | (2006.01) |
| *C07J 53/00* | (2006.01) |
| *C07J 51/00* | (2006.01) |

(52) U.S. Cl.
CPC ........... *A61K 31/5685* (2013.01); *C07J 1/0011* (2013.01); *C07J 41/0005* (2013.01); *A61K 45/06* (2013.01); *C07J 75/00* (2013.01); *C07J 53/001* (2013.01); *C07J 51/00* (2013.01)
USPC ........... 514/177; 514/170; 514/178; 514/179; 552/615

(58) Field of Classification Search
None
See application file for complete search history.

(56) References Cited

U.S. PATENT DOCUMENTS

| | | |
|---|---|---|
| 2,744,120 A | 5/1956 | Fried |
| 3,032,565 A | 8/1960 | Dodson |
| 4,235,893 A | 11/1980 | Brodie |
| 4,289,762 A | 9/1981 | Metcalf |
| 4,322,416 A | 3/1982 | Metcalf |
| 4,473,564 A | 9/1984 | de Winter |
| 4,808,578 A | 2/1989 | Faustini |
| 4,808,616 A | 2/1989 | Buzzetti |
| 4,904,650 A | 2/1990 | Buzzetti |
| 4,978,672 A | 12/1990 | Bowman |
| 5,073,574 A | 12/1991 | Lang |
| 5,112,845 A | 5/1992 | Bowman |
| 5,352,795 A | 10/1994 | Bowman |
| 5,426,196 A | 6/1995 | Fang |
| 5,457,209 A | 10/1995 | Differding |
| 5,473,078 A | 12/1995 | Bowman |
| 5,703,109 A | 12/1997 | Karjalainen |
| 5,866,558 A | 2/1999 | Abul-Hajj |
| 5,962,495 A | 10/1999 | Karjalainen |
| 6,586,417 B1 | 7/2003 | Abraham |

FOREIGN PATENT DOCUMENTS

| | | |
|---|---|---|
| DE | 3338212 A1 | 4/1985 |
| EP | 0737689 | 10/1966 |
| EP | 0300062 | 11/1988 |
| EP | 11766695.8 | 4/2014 |
| JP | 63-045294 | 2/1998 |
| JP | 07-215992 | 1/2007 |
| WO | 8805781 | 8/1988 |
| WO | 9419365 | 1/1994 |
| WO | 9404554 | 3/1994 |
| WO | 9501366 | 12/1995 |
| WO | 2007041564 | 4/2007 |
| WO | 2011127232 | 10/2011 |
| WO | 2012/031501 | 10/2012 |

OTHER PUBLICATIONS

Numazawa et al. Probing the binding pocket of the activee site of aromatese with 6-ether or 6-ester substituted androst-4-ene 3,17-diones and their dienee and triene analogs. Steroids 2000, vol. 65 pp. 871-882.*
Shibuya et al. Intratumoral concentration of sex steroids and expression of sex steroid-producing enzymes in ductal carcinoma in situ of human breast. Endocrine-Related Cancer (2008) 15:113-124.
Brzozowski et al. Molecular basis of agonism and antagonism in the oestrogen receptor. Nature. 1997; 389 (6652):753-758.
Marcotte et al. Design of Mechanism-based Inactivators of Human Placenta Aromatase. Cancer Res. 1982;42:3322s-3326s.
Numazawa et al. Studies on the catalytic function of aromatase: aromatization of 6-alkoxy-substituted androgens. J Steroid Biochem Mol Biol. 2002, 82(1):65-73.
Ghosh et al. Novel aromatase inhibitors by structure-guided design. J Med Chem. 2012, 55(19):8464-76.
Numazawa et al. Enzymic aromatization of 6-alkyl-substituted androgens, potent competitive and mechanism-based inhibitors of aromatase, Biochem J. 1998, 329 (Pt 1):151-6.
Abul-Haji et al. Synthesis and evaluation of 4-substituted-4-androstene-3,17-dione derivatives as aromatase inhibitors. J Steroid Biochem Mol Biol. 1995. 54(3-4):111-9.

(Continued)

*Primary Examiner* — Melenie McCormick
*Assistant Examiner* — Taina D Matos Negron
(74) *Attorney, Agent, or Firm* — Emory Patent Group

(57) ABSTRACT

The disclosure relates to novel C4 and C6 substituted androst-4-ene diones as well as andros-1,4-diene diones and derivatives thereof, their process of preparation, pharmaceutical compounds containing them, and the use of said compounds for the treatment of hormone-related disorders in mammals. This includes hormone-dependent cancers, particularly those caused by elevated levels of estrogen and its intermediates. These compounds can also be used in the treatment of other hormone-related disorders, including benign prostatic hyperplasia, cardiovascular disease, and neurodegenerative disorders.

10 Claims, 7 Drawing Sheets

(56) References Cited

OTHER PUBLICATIONS

Marsh et al. Aromatase Inhibitors. Synthesis and Biological Activity of Androstenedione Derivatives J. Med. Chem. 1985, 28, 788-795.

Nabholtz et al. Comparative review of anastrozole, letrozole and exemestane in the management of early breast cancer Expert Opin. Pharmacother. (2009) 10(9):1435-1447.

Mamounas et al. Benefit From Exemestane As Extended Adjuvant Therapy After 5 Years of Adjuvant Tamoxifen J. Clin. Oncology, 26(12): 1965-1971 2008.

Hutchinson, Can exemestane improve adjuvant treatment for postmenopausal women with primary breast cancer? Nature Clinical Practice Oncology (2004) 1, 24-25.

Davis & Manning Catalytic C—H functionalization by metal carbenoid and nitrenoid insertion Nature 451, 417-424 (2008).

Yue et al. Regioselectivity in Lewis acids catalyzed X—H (O, S, N) insertions of methyl styryldiazoacetate with benzyl alcohol, benzyl thiol, and aniline. Tetrahedron Letters 48 (2007) 3975-3977.

Morton et al. Convenient method for the functionalization of the 4- and 6-positions of the androgen skeleton Chem. Commun. 2012, 48, 5838-5840.

Moreau & Sorensen Classical carbonyl reactivity enables a short synthesis of the core structure of acutumine Tetrahedron 2007, 63, 6446-6453.

Demarco Pyridine-Induced Solvent Shifts in the Nuclear Magnetic Resonance Spectra of Hydroxylic Compounds Journal of the American Chemical Society/90:20/1968.

Numazawa et al. Probing the binding pocket of the active site of aromatase with 6-ether or 6-ester substituted androst-4-ene-3,17-diones and their diene and triene analogs. Steroids. 2000, vol. 65, pp. 871-882.

Numazawa et al. A- or B-Ring-subsituted derivatives of androst-4-ene-3,6,17-trione as aromatase inhibitors. Structure-activity relationships, Steroids, 1994, vol. 59, pp. 579-585.

Lesuisse et al. Synthesis and Evaluation of a New Series of Mechanism-Based Aromatase Inhibitors J. Med. Chem. 1992, 35, 1588-1597.

Sharma et al. Synthesis and evaluation of novel 4-amino-4,6-androstadiene-3, 17-dione: An analog of formestane, Bioorganic & Medicinal Chemistry Letters 18 (2008) 5563-5566.

Terasawa et al. 6-Substituted and 19-Substituted Androst-4-Ene-3,17-Dione Derivatives As Potential Aromatase Inhibitors, Steroids (1987) 50:4-6.

\* cited by examiner

HDDG-016

HDDG-017

HDDG-018

HDDG-019

HDDG-020

HDDG-021

HDDG-022

HDDG-023

HDDG-024

HDDG-045

HDDG-047

HDDG-048

HDDG-049

HDDG-050

HDDG-051

HDDG-052

HDDG-053

HDDG-054

HDDG-055

HDDG-056

SUBSTITUTED ANDROST-4-ENE DIONES

CROSS-REFERENCE TO RELATED APPLICATIONS

This application claims priority to U.S. Provisional Application No. 61/322,062, filed Apr. 8, 2010, which is incorporated herein by reference in its entirety.

ACKNOWLEDGEMENTS

This invention was made with government support under Grant No. R01GM086893 awarded by the National Institutes of Health. The government has certain rights in the invention.

FIELD

This disclosure provides compounds and methods for selective inhibition of the aromatase enzyme, useful in the treatment of hormone-related disorders, including but not limited to hormone-dependent cancers and other hormone-related disorders.

BACKGROUND

Estrogens are essential regulators of many physiological processes including maintenance of the female sexual organs, the reproductive cycle and numerous neuroendocrine functions. Importantly, these hormones also play crucial roles in several disease states, particularly in hormone-dependent cancers, such as breast, endometrial, pancreatic, and ovarian carcinomas. Worldwide, breast cancer is the leading cause of death from cancer among women, with more than 500,000 estimated to have died from the disease in 2009. Furthermore, systemic estrogen levels are key indicators of breast cancer recurrence [*Breast Cancer,* 15:270-277 (2008)], implicating estrogen in the progression of debilitating and life-threatening diseases.

Through binding to their target estrogen Receptor (ER), estrogen promotes both cell proliferation as well as tumor invasiveness [*Genome Biol.,* 5(9): R66 (2004)]. Given that the majority of breast, endometrial, and ovarian carcinomas express ERs and are thus potentially sensitive to the growth promoting effects of estrogens, current treatment strategies for ER+ cancers are largely concerned with the inhibition of the estrogen synthesis pathway.

Recent studies have demonstrated that estrogens are produced in ER+ cancers by several enzymes. Among these enzymes in the estrogen biosynthetic pathway, aromatase is considered a crucial enzyme for estrogen synthesis. High concentrations of circulating inactive steroids, such as androstenedione, are major precursors to intratumoral estrogen production.

Aromatase is a member of the P450 mono-oxygenase family and is directly responsible for the conversion of androgens (androstenedione and testosterone) to estrogens (estrone and estradiol, respectively), through oxidative removal of the C19 methyl group and subsequent aromatization. A majority of ER+ cancers have aromatase activities that are comparable with or greater than those found in other tissues, and aromatase mRNA levels are typically increased in ER+ carcinomas relative to nonmalignant tissue [*J. Clin. Endocrinol. Metab.,* 81:2344-9 (1996); *Endocr. Relat. Cancer.,* 12:701-20 (2005)]. For example, it has been shown that the gene for aromatase is over expressed in >75% of breast cancer lines, which results in the disease tissue being saturated in estrogens, promoting the growth of the cancerous cells. Not only are expression levels increased in $ER^+$ cancer cells, but they are also increased in surrounding cells, such as adipose tissue and stromal cells [*Hum. Pathol.,* 5:530-3 (1994); *J. Clin. Endocrinol. Metab.,* 79: 627-32 (1994); *J. Steroid Biochem. Mol. Biol.,* 95: 35-9 (2005)]. Furthermore, aromatase mRNA levels have been shown to correlate with the level of breast tumor invasiveness; where they are highest in invasive carcinoma, modest in noninvasive carcinoma, and lowest in normal tissue [*Endocr. Relat. Cancer.,* 15: 113-24 (2008)]. Thus, the aromatase enzyme is a key target in the inhibition of the estrogen biosynthesis pathway. Inhibition of aromatase has been demonstrated to significantly reduce re-growth of certain cancer after initial treatments [*Lancet Oncol.,* 9(1):8-10 (2008)].

Aromatase inhibitors are an established alternative treatment option to other forms of estrogen regulation [*J. Steroid Biochem. Mol. Bio.,* 95: 75-81 (2005)], including molecules such as tamoxifen that are known to inhibit estrogen signaling [*Mol Endocrinol.* 9: 659-669 (1995); *Nature* 387: 733-736 (1997)]. Substances that have been reported to at least partially inhibit aromatase action include, for example, $\Delta^1$-testololactone (U.S. Pat. No. 2,744,120), 4-hydroxyandrost-4-ene-3,17-dione and esters thereof (for example, U.S. Pat. No. 4,235,893), 10-(1,2-propadienyl)-estr-4-ene-3,17-dione (U.S. Pat. No. 4,289,762), 10-(2-propynyl)-estr-4-ene-3,17-dione [*J. Am. Chem. Soc.,* 103: 3221 (1981) and U.S. Pat. No. 4,322,416], 19-thioandrostene derivatives (Europ. Pat. Appl. 100566), androsta-4,6-diene-3,17-dione, androsta-1,4,6-triene-3,17-dione (G.B. Pat. Appl. 2,100,601A), androsta-1,4-diene-3,17-dione [*Cancer Res.,* 42: 3327 (1982)], 6-substituted androsta-1,4-diene-3,17-diones (U.S. Pat. No. 4,808,616), substituted androsta-1,4-diene-3,17-diones (U.S. Pat. No. 4,904,650), alpha-heterocyclic substituted tolunitriles (U.S. Pat. Nos. 4,978,672; 5,112,845; 5,352,795; 5,473,078), tetrazolyl substituted benzonitriles (U.S. Pat. No. 5,073,574), diaryl methanes (U.S. Pat. No. 5,426,196), 4-[alpha(cyanophenyl)-1-(1,2,3-triazolyl)methyl]-benzonitrile (U.S. Pat. No. 5,457,209), heterocyclic diarylalkyl compounds (U.S. Pat. Nos. 5,703,109; 5,962,495). Although several of these compounds are able to inhibit aromatase, their binding activities are not specific; as a result, they cause a number of off target effects in patients [*Expert Opin. Pharmacother.,* 10(9):1435-47 (2009)].

Certain compounds have been found to interact with heightened specificity to the aromatase enzyme. Exemestane (6-methylenandrost-1,4-diene-3,17-dione), which is described in U.S. Pat. No. 4,808,616, is structurally related to the natural substrate androstenedione and is initially recognized by the aromatase enzyme as a false substrate thus competing with androstenedione at the active site of the enzyme. The compound is transformed to an intermediate that binds irreversibly to the enzyme, causing its inactivation (also known as suicide inhibition). Although exemestane is more selective than its predecessors in the inhibition of aromatase, its use has also been shown to result in potentially debilitating off target effects. For example, some studies have demonstrated that the sex hormone binding globulin, a protein that regulates the bioavailability of sex hormones, is dysregulated in patients taking exemestane [*Clin. Breast Cancer,* 9(4): 219-24 (2009)]. Yet other studies have demonstrated that Exemestane can interfere with calcium homeostasis [*Curr. Oncol. Rep.,* 6(4): 277-84. (2004); *The Lancet Oncology,* 8(2): 119-127 (2007); *Clin. Breast Cancer,* 8(6): 527-32 (2008)]. Most importantly, however, is that exemestrane use has been associated with additional side effects, such as severe hepatotoxicity, that are not observed with other aromatase inhibitors [*Breast Cancer Res. Treat.*, October 16. (Epub ahead of print) (2009)].

Additional compounds related to exemestane, include (S)-6-methyloxaalkyl exemestane derivatives (PCT Appl. No. WO 2007041564), fluorinated 4-aminoandrostadienones (PCT Appl. No. WO 9419365), fluorinated 6-methyleneandrosta-1,4-dien-3-ones (PCT Appl. No. WO 9501366), and androst-4-eno[4,5-b]pyrroles (PCT Appl. No. WO 9404554). A range of 6-alkoxy and 6-keto steroids have been synthesized by reaction of an unsubstituted steroid with a suitable lower alcohol such as methanol or ethanol together with a cupric halide, where the halide can be either chloride or bromide (U.S. Pat. No. 3,032,565). Steroid derivatives were also synthesized by reaction of the epoxy derivatives with a compound such as sodium thiocyanate and subjecting the reaction product to a dehydration reaction (Japanese Pat. No, 63-045294, 1998). A range of 6 and 7 substituted androst-1,4-diene derivatives were obtained by converting a suitable bromo derivative to the corresponding thiol followed by further alkylation or acylation (Japanese Pat. No., 07-215992). A range of C6 substituted androst-4-ene-3,17-diones were formed by bringing the unsubstituted precursor andros-4-ene-3,17-dione into contact with certain microorganisms (Japanese Pat. No. WO 1988/05781).

In probing the binding pocket of the active site of aromatase, Numazawa et al. synthesized and tested a range of 6-ester and 6-ether substituted androst-4-ene-3,17-diones as well as their 1,4-diene and 1,4,6-triene analogues. The 6β-methoxy and 6β ethoxy androsta-1,4-diene-3,17-dione derivatives were found to be suicide substrates of aromatase (M. Numazawa, M Ando and R. Zennyoji, *J Steroid Biochem Molec Biol*. 2002, 82:65-73 and Numazawa et al., Biochem J., 1998, 3299(1), 151-156).

In their evaluation of 4-substituted-4-androstene-3,17-dione derivatives as, Abul-Hajj et al., showed that aromatase has a hydrophobic pocket in the active site around the C4α region of androstenedione. (Y. J. Abul-Hajj, X-P, Liu and M. Hedge, *J Steroid Biochem Molec Biol*. 1995, 54:111-119). Marsh et al. showed that esterification of the 4-hydroxy analogues generally reduced activity but conjugation of the 3-keto 4-ene system to produce 4-hydroxy-4,6-androstadiene-3,17-dione caused more rapid inactivation of aromatase in rat ovarian microsomes than the 4-hydroxyandrostenedione (D. A. Marsh, H. J. Brodie, W. Garrett, C-H, Tsai-Morris and A. M. H. Brodie, *J. Med. Chem.*, 1985, 28:788-795). A variety of ester and ether derivatives of 4-hydroxy 4-androstenedione were suggested as means of regulating athletic function in humans. (U.S. Pat. No. 6,586,417 B1).

SUMMARY

Because of the side effects associated with the use of existing aromatase inhibitors, there exists a need for new compounds that are capable of specifically inhibiting the aromatase enzyme with reduced off-target effects. It is thus an object of this disclosure to provide compounds, methods of preparation thereof and methods for treatment or prophylaxis of hormone-related disorder, and in particular certain estrogen-related disorders including, but not limited to, breast, endometrial, or ovarian cancers. It is a further object of the disclosure to provide compounds and methods of treatment or prophylaxis of other hormone, and in particular estrogen-related disorders, including benign prostatic hyperplasia, cardiovascular disease, or neurodegenerative disorders.

The present disclosure is directed to certain C4 and C6 substituted androst-4-ene diones as well as andros-1,4-diene diones and derivatives thereof, and the use of these compounds and derivatives as aromatase inhibitors, for example in the treatment of endocrine diseases, hormonal disorders, proliferative diseases such as cancer, and other estrogen-related pathologies.

In certain embodiments, the disclosure relates to compounds disclosed herein comprising one or more substituents. Compounds, methods of their preparation and pharmaceutical compositions and methods of aromatase inhibition or treatment or prophylaxis of a hormone-related disorder including certain compounds of Formula A are provided

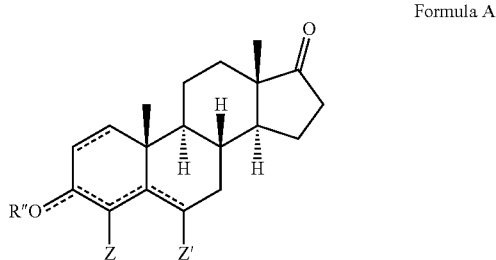

Formula A or pharmaceutically acceptable salts, ester, prodrugs or derivatives thereof, wherein

- - - - - represents a double bond either absent or present and R" is absent when the double bond is present or is H when the double bond is absent;

Z' is absent or is OR' and Z is absent or is OR, wherein when Z' is absent, Z is OR and when Z is absent Z' is OR';

R and R' are independently selected from H, a straight chained or branched $C_1$ to $C_8$ alkyl group, an alkenyl group, an alkynyl group, an alkanoyl group and an aroyl group, or substituted derivatives thereof. In certain embodiments, R and R' are independently selected from a substituted alkenyl or alkynyl group. The substituents can be any substituent known to one of ordinary skill, but in certain embodiments are selected from H, OH, phenyl, benzyl, naphthyl, substituted aryl, $C_1$ to $C_8$ alkyl group. Compounds of Formula A can comprise either two or three double bonds at the positions indicated.

In certain embodiments, - - - - - represents a bond either absent or present as a double bond and R" is absent when the double bond is present or is H when the bond is absent;

Z' is hydrogen or is OR' and Z is hydrogen or is OR, wherein when Z' is hydrogen, Z is OR and when Z is hydrogen Z' is OR';

R and R' are independently selected from an alkyl, alkenyl, or alkynyl group optionally substituted with one or more substituents.

In certain embodiments, R' is an alkyl substituted with an optionally substituted aryl group. In certain embodiments, R' is alkenyl or alkynyl optionally substituted with one or more substituents. Typically the substituent is selected from OH, phenyl, benzyl, naphthyl, substituted aryl, or $C_1$ to $C_8$ alkyl group. In some embodiments, the substituent is selected from aryl, substituted aryl, heterocyclo, substituted heterocyclo, carbocyclo, substituted carbocyclo, or halo. In some embodiments, the substituent is selected from alkoxy (optionally substituted), aryloxy (optionally substituted), alkylester (optionally substituted), arylester (optionally substituted), alkanoyl (optionally substituted), or aryol (optionally substituted).

In some embodiments, the compound is (6R,8R,9S,10R, 13S,14S)-10,13-dimethyl-6-(pentyloxy)-7,8,9,10,11,12,13, 14,15,16-decahydro-3H-cyclopenta[a]phenanthrene-3,17 (6H)-dione;

(6R,8R,9S,10R,13S,14S)-10,13-dimethyl-6-((E)-pent-2-en-1-yloxy)-7,8,9,10,11,12,13,14,15,16-decahydro-3H-cyclopenta[a]phenanthrene-3,17(6H)-dione;

(6R,8R,9S,10R,13S,14S)-10,13-dimethyl-6-((Z)-pent-2-en-1-yloxy)-7,8,9,10,11,12,13,14,15,16-decahydro-3H-cyclopenta[a]phenanthrene-3,17(6H)-dione;

(6R,8R,9S,10R,13S,14S)-6-(cinnamyloxy)-10,13-dimethyl-7,8,9,10,11,12,13,14,15,16-decahydro-3H-cyclopenta[a]phenanthrene-3,17(6H)-dione;

(6R,8R,9S,10R,13S,14S)-10,13-dimethyl-6-(3-phenylpropoxy)-7,8,9,10,11,12,13,14,15,16-decahydro-3H-cyclopenta[a]phenanthrene-3,17(6H)-dione;

(6R,8R,9S,10R,13S,14S)-10,13-dimethyl-6-((5-phenylpentyl)oxy)-7,8,9,10,11,12,13,14,15,16-decahydro-3H-cyclopenta[a]phenanthrene-3,17(6H)-dione;

(6R,8R,9S,10R,13S,14S)-10,13-dimethyl-6-(oct-2-yn-1-yloxy)-7,8,9,10,11,12,13,14,15,16-decahydro-3H-cyclopenta[a]phenanthrene-3,17(6H)-dione; and (6R,8R,9S,10R,13S,14S)-10,13-dimethyl-6-(pent-2-yn-1-yloxy)-7,8,9,10,11,12,13,14,15,16-decahydro-3H-cyclopenta[a]phenanthrene-3,17(6H)-dione.

In certain embodiments, the disclosure relates to pharmaceutical compositions comprising a compound disclosed herein and a pharmaceutically acceptable excipient.

In certain embodiments, the disclosure relates to methods of treating a hormone-related disorder comprising administering a pharmaceutical composition disclosed herein to a subject in need thereof. The subject may be diagnosed with, at risk of, or exhibiting symptoms of a hormone-related disorder. The hormone related disorder may be osteoporosis, endometriosis, breast cancer, benign breast cancer, uterine cancer, ovarian cancer, polycystic ovarian disease, prostate cancer, or benign prostatic hyperplasia (BPH). The pharmaceutical composition may be administered in combination with a second pharmaceutical agent such as estrogen.

In certain embodiments, the disclosure relates to the use of compounds disclosed herein in the production of a medicament for the treatment of a hormone related disorder.

Methods of preparation of compounds of formula A are provided including: (i) substitution of a 1,4-diene-steroid or 4-ene-steroid; (ii) deconjugation to afford a diazo-precursor; and (iii) reaction in the presence of either $Rh_2(S\text{-}DOSP)_4$ to afford a 4-substituted steroid, or AgOTf to furnish 6-substituted steroid.

In certain embodiments, the disclosure relates to processes for producing compounds disclosed herein, comprising mixing (8R,9S,10R,13S,14S)-4-diazo-10,13-dimethyl-7,8,9,10,11,12,13,14,15,16-decahydro-3H-cyclopenta[a]phenanthrene-3,17(4H)-dione, an alcohol (R'—OH), and a metal catalyst under conditions such that a compound of Formula A is formed. The metal catalyst may be a silver catalyst or a of dirhodium(II) catalyst.

Other compositions, methods, features, and advantages of the present disclosure will be or become apparent to one with skill in the art upon examination of the following drawings and detailed description. It is intended that all such additional compositions, methods, features, and advantages be included within this description, be within the scope of the present disclosure, and be protected by the accompanying claims.

DETAILED DESCRIPTION OF THE DISCLOSURE

Figure 1:
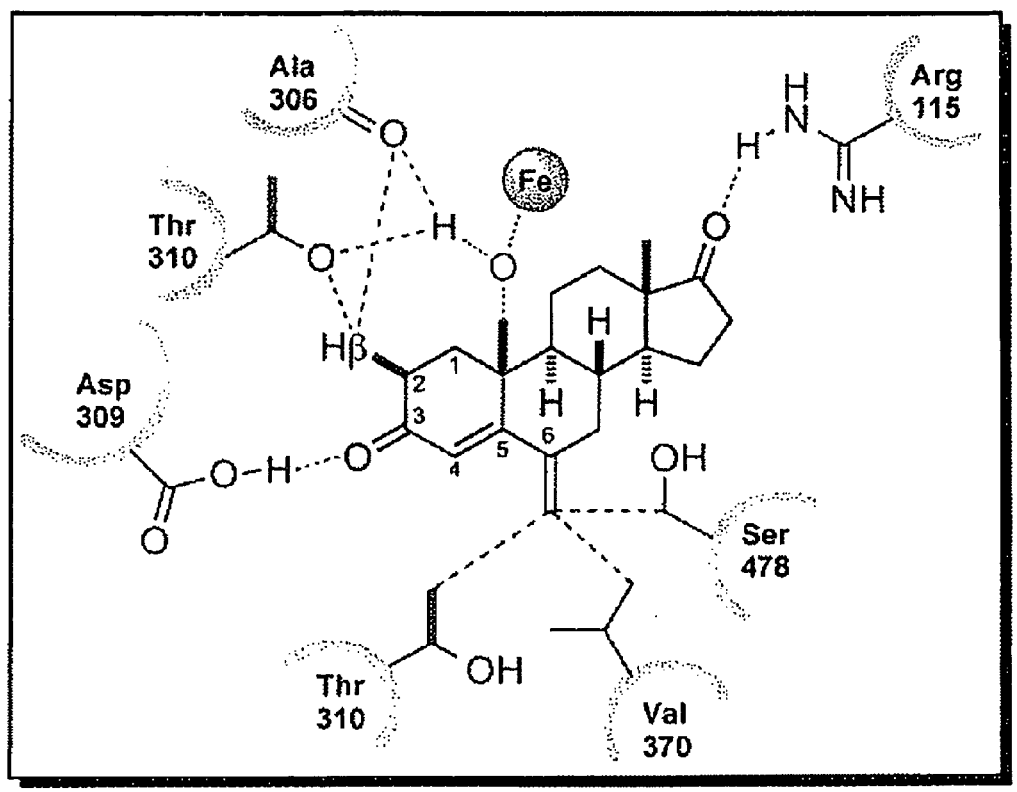
FIG. 1 illustrates the interaction of exemestane with the crystallized active site of aromatase.
Figure 2:
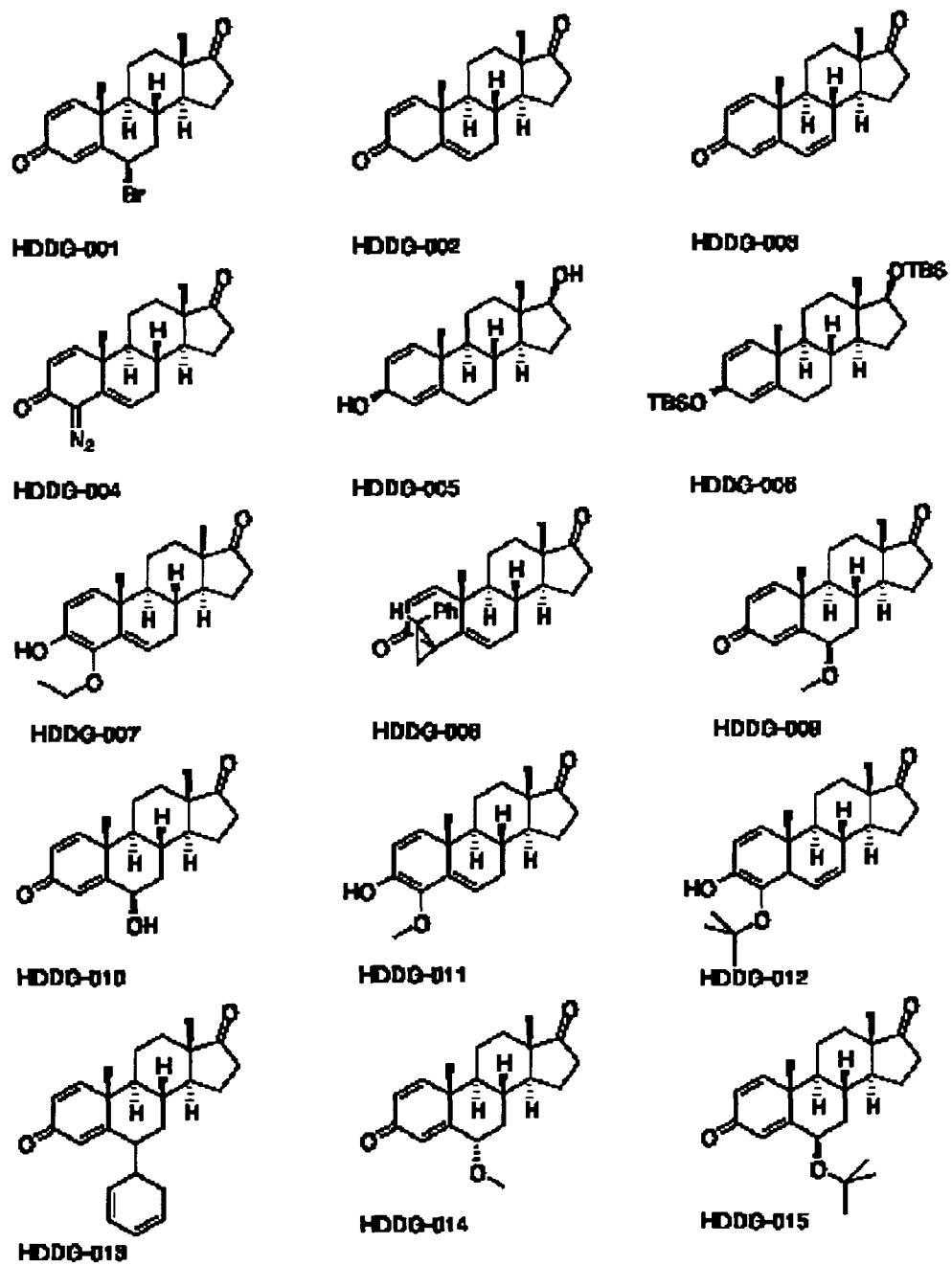
FIG. 2 illustrates the chemical formula of certain embodiments of the disclosure.
Figure 3:
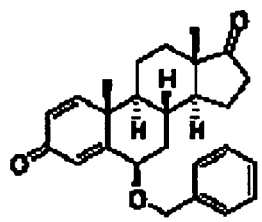
FIG. 3 illustrates the chemical formula of certain embodiments of the disclosure.
Figure 3:
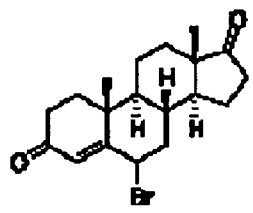
Figure 3:
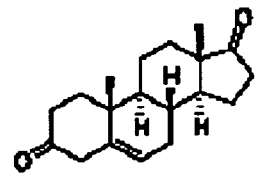
Figure 3:
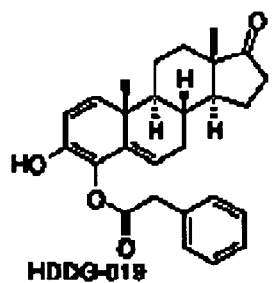
Figure 3:
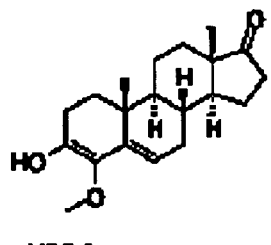
Figure 3:
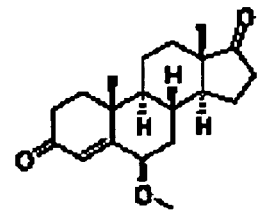
Figure 3:
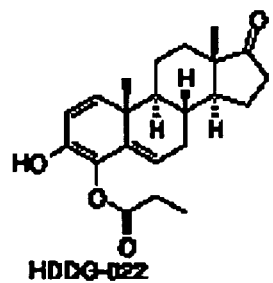
Figure 3:
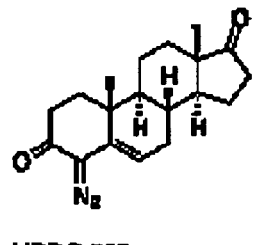
Figure 3:
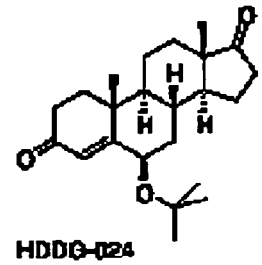
Figure 4:
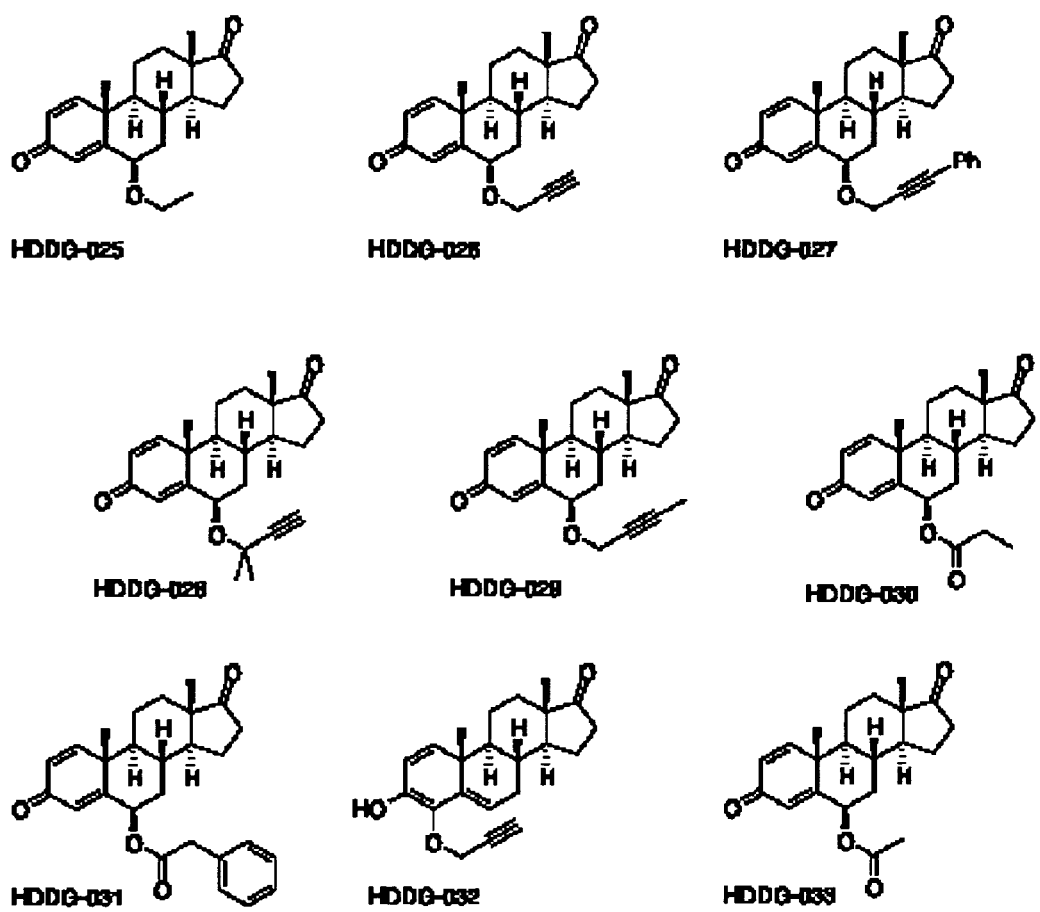
FIG. 4 illustrates the chemical formula of certain embodiments of the disclosure.
Figure 5:
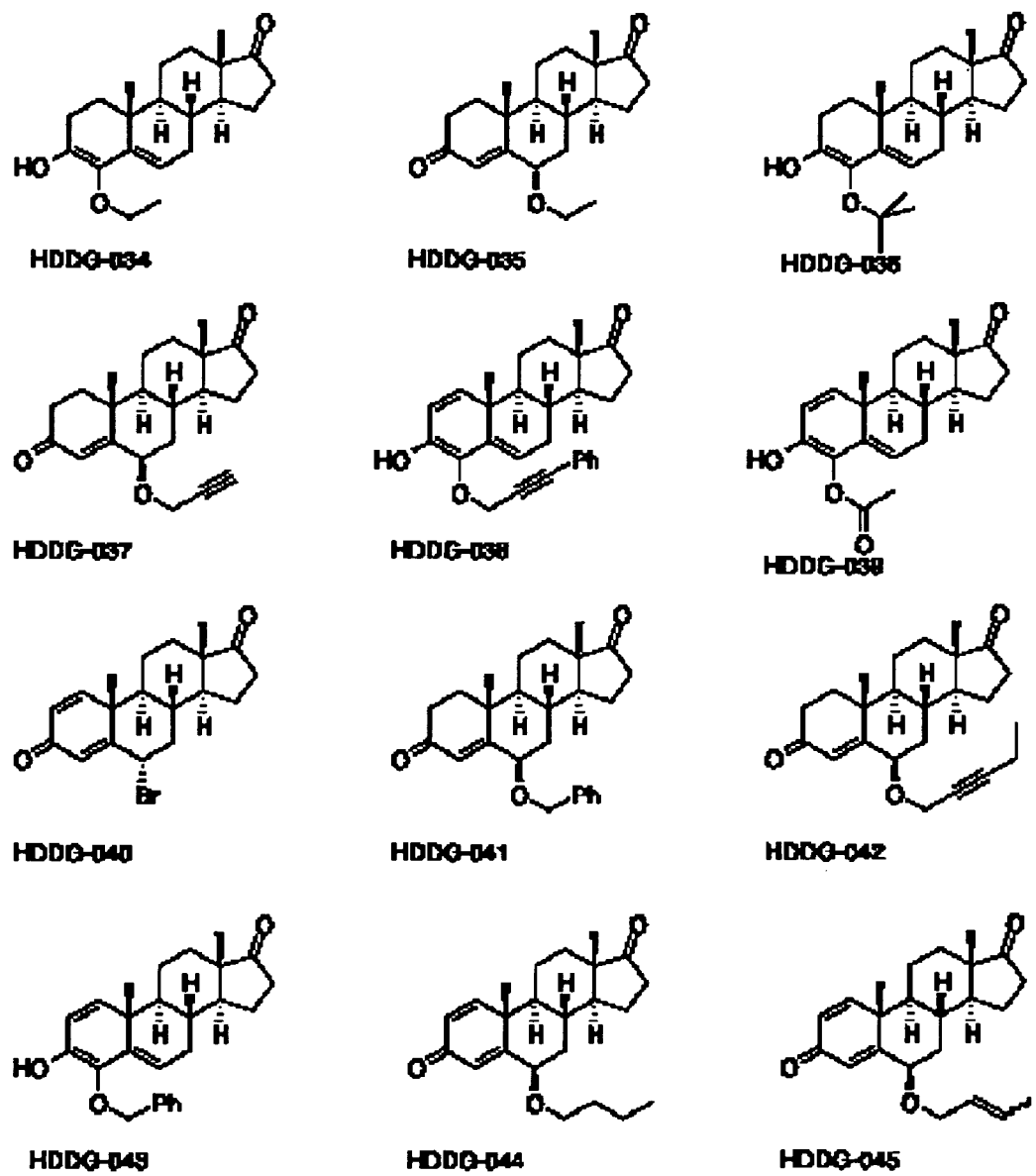
FIG. 5 illustrates the chemical formula of certain embodiments of the disclosure.
Figure 6:
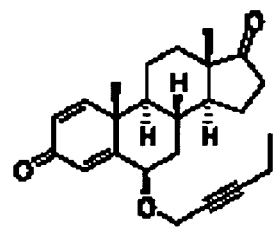
FIG. 6 illustrates the chemical formula of certain embodiments of the disclosure.
Figure 6:
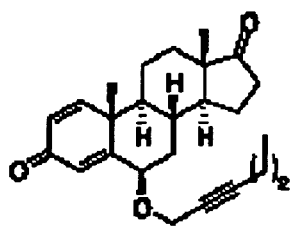
Figure 6:
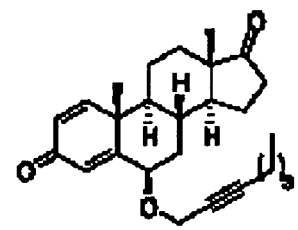
Figure 6:
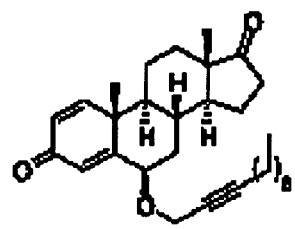
Figure 6:
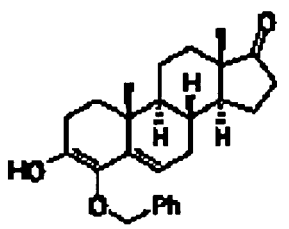
Figure 6:
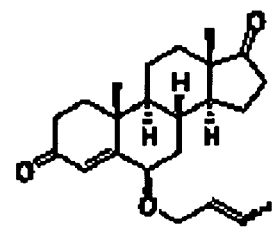
Figure 6:
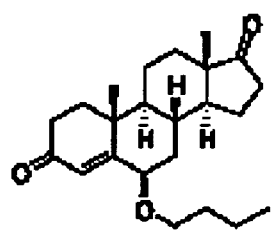
Figure 6:
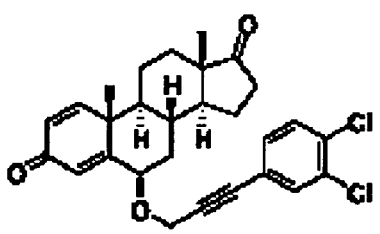
Figure 6:
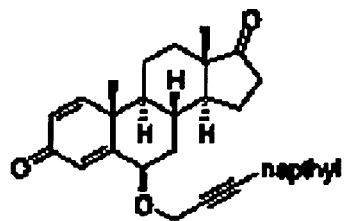
Figure 6:
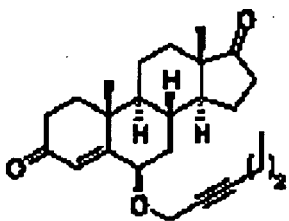
Figure 6:
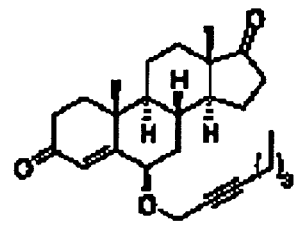
Figure 7:
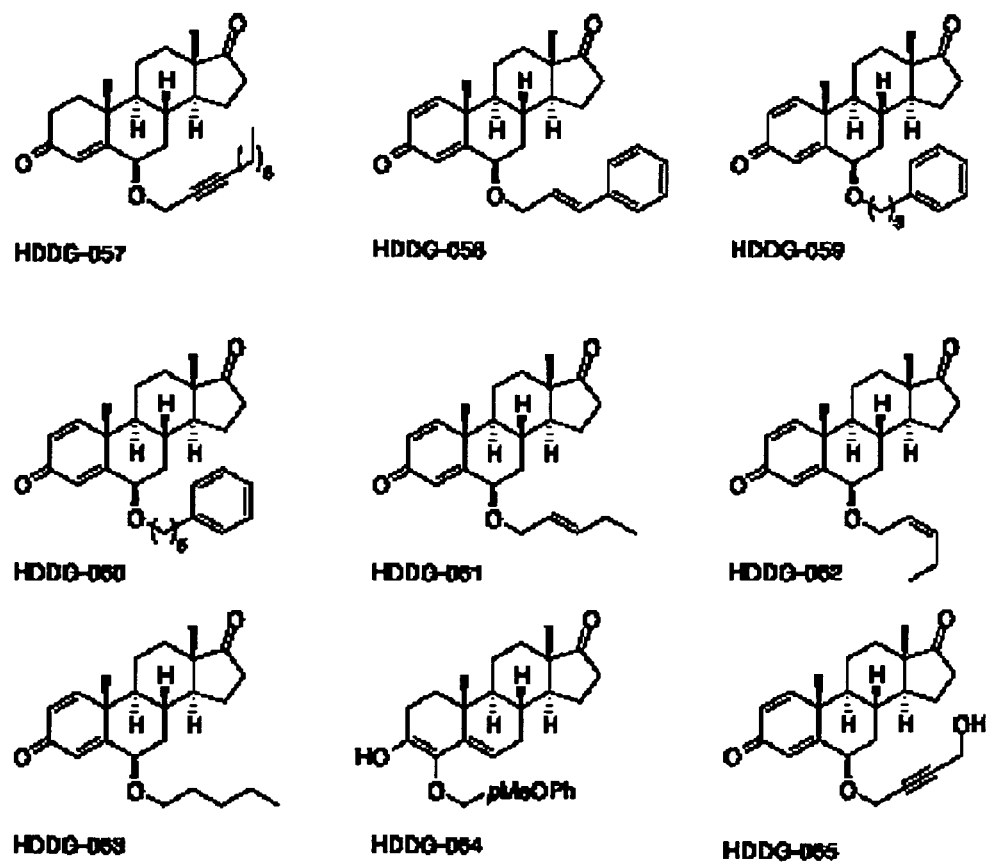
FIG. 7 illustrates the chemical formula of certain embodiments of the disclosure.

The present disclosure may be understood more readily by reference to the following detailed description and the examples included therein. Before the present compounds, compositions and methods are disclosed and described, it is to be understood that this disclosure is not limited to specific pharmaceutical carriers, or to particular pharmaceutical formulations or administration regimens, as such may, of course, vary. It is also to be understood that the terminology used herein is for the purpose of describing particular embodiments only and is not intended to be limiting.

DEFINITIONS

The term "aromatase inhibitor" means a compound, pharmaceutically acceptable salt, prodrug, or derivative thereof that inhibits the biological activity of aromatase, interferes with the estrogen biosynthesis pathway, or down regulates expression or availability of estrogen in a cell or organism.

The term "inhibits aromatase activity" as used herein refers to a 1%, 5%, 10%, 25%, 50%, 75%, 90%, or 100% decrease in the ability of aromatase to convert androgens into estrogen, measured in any cell, tissue, or extract, relative to untreated control samples. This also refers to the bioavailability of estrogen in treated cells, tissues, or extracts, relative to untreated control samples.

The term "estrogen-related pathology, disease, or condition" means a pathology that is caused in part, either directly or indirectly, by conditions of elevated typical physiological amounts of estrogen.

The term "derivative" means a modification to the disclosed compounds including but not limited to hydrolysis, reduction, or oxidation products of the disclosed compounds. Hydrolysis, reduction, and oxidation reactions are known in the art.

The term "therapeutically effective amount" as used herein refers to that amount of the compound being administered which will relieve to some extent one or more of the symptoms of the disorder being treated. In reference to cancer or pathologies related to increased cell division, a therapeutically effective amount refers to that amount which has the effect of (1) reducing the size of a tumor, (2) inhibiting (that is, slowing to some extent, preferably stopping) aberrant cell division, for example cancer cell division, (3) preventing or reducing the metastasis of cancer cells, (4) relieving to some extent (or, preferably, eliminating) one or more symptoms associated with a pathology related to or caused in part by unregulated or aberrant cellular division, including for example, cancer, and/or (5) to prevent the chain of events downstream of estrogen biosynthesis which leads to the pathology.

"Pharmaceutically acceptable salt" refers to those salts which retain the biological effectiveness and properties of the free bases and which are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

A "pharmaceutical composition" refers to a mixture of one or more of the compounds described herein, or pharmaceutically acceptable salts thereof, with other chemical components, such as physiologically acceptable carriers and excipients. One purpose of a pharmaceutical composition is to facilitate administration of a compound to an organism.

As used herein, a "pharmaceutically acceptable carrier" refers to a carrier or diluent that does not cause significant irritation to an organism and does not abrogate the biological activity and properties of the administered compound.

An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

"Treating" or "treatment" of a disease includes preventing the disease from occurring in an animal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease). With regard to cancer or hyperplasia, these terms simply mean that the life expectancy of an individual affected with a cancer will be increased or that one or more of the symptoms of the disease will be reduced. With regard to cardiovascular disease or related conditions, these terms simply mean that the life expectancy of an individual affected with cardiovascular disease will be increased or that one or more of the symptoms of the disease will be reduced. With regard to neurodegenerative disease or related conditions, these terms simply mean that the life expectancy of an individual affected with neurodegenerative disease will be increased or that one or more of the symptoms of the disease will be reduced.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N. J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, *Curr. Pharm. Design.* 5(4):265-287; Pauletti et al. (1997). Improvement in peptide bioavailability: Peptidomimetics and Prodrug Strategies, *Adv. Drug. Delivery Rev.* 27:235-256; Mizen et al. (1998). The Use of Esters as Prodrugs for Oral Delivery of β-Lactam antibiotics, *Pharm. Biotech.* 11:345-365; Gaignault et al. (1996). Designing Prodrugs and Bioprecursors I. Carrier Prodrugs, *Pract. Med. Chem.* 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, *Eur. J. Drug Metab. Pharmacokinet.*, 15(2): 143-53; Balimane and Sinko (1999). Involvement of multiple transporters in the oral absorption of nucleoside analogues, *Adv. Drug Delivery Rev.*, 39(1-3):183-209; Browne (1997). Fosphenyloin (Cerebyx), *Clin. Neuropharmacol.* 20(1): 1-12; Bundgaard (1979). Bioreversible derivatization of drugs—principle and applicability to improve the therapeutic effects of drugs, *Arch. Pharm. Chemi.* 86(1): 1-39; H. Bundgaard, ed. (1985) Design of Prodrugs, New York: Elsevier; Fleisher et al. (1996). Improved oral drug delivery: solubility limitations overcome by the use of prodrugs, *Adv. Drug Delivery Rev.* 19(2): 115-130; Fleisher et al. (1985). Design of prodrugs for improved gastrointestinal absorption by intestinal enzyme targeting, *Methods Enzymol.* 112: 360-81; Farquhar D, et al. (1983). Biologically Reversible Phosphate-Protective Groups, *J. Pharm. Sci.*, 72(3): 324-325; Han, H. K. et al. (2000). Targeted prodrug design to optimize drug delivery, *AAPS PharmSci.*, 2(1): E6; Sadzuka Y. (2000). Effective prodrug liposome and conversion to active metabolite, *Curr. Drug Metab.*, 1(1):31-48; D. M. Lambert (2000) Rationale and applications of lipids as prodrug carriers, *Eur. J. Pharm. Sci.*, 11 Suppl 2:S15-27; Wang, W. et al. (1999) Prodrug approaches to the improved delivery of peptide drugs. *Curr. Pharm. Des.*, 5(4):265-87.

The term "alkyl" refers to straight or branched chain hydrocarbon groups having 1 to 12 carbon atoms, preferably 1 to 8 carbon atoms, such as methyl, ethyl, n-propyl, i-propyl, n-butyl, i-butyl, t-butyl, pentyl, hexyl, heptyl, octyl, and the like. The term "substituted alkyl" refers to alkyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), and the like.

The term "alkoxy" means an alkyl group linked to oxygen thus: R—O—. In this function, R represents the alkyl group. An example would be the methoxy group $CH_3O$—.

The term "alkenyl" refers to straight or branched chain hydrocarbon groups having 2 to 12 carbon atoms, and at least one double carbon to carbon bond (either cis or trans), such as ethenyl.

The term "substituted alkenyl" refers to alkenyl groups substituted with one or more groups, preferably selected from aryl, substituted aryl, heterocyclo, substituted heterocyclo, carbocyclo, substitute α carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), and the like.

The term "alkynyl" refers to straight or branched chain hydrocarbon groups having 2 to 12 carbon atoms, and at least one triple carbon to carbon bond, such as ethynyl.

The term "substituted alkynyl" refers to alkynyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), and the like.

The term "aryl" refers to an aromatic homocyclic (i.e., hydrocarbon) mono-, bi- or tricyclic ring-containing groups preferably having 6 to 12 members such as phenyl, naphthyl and biphenyl. Phenyl is a preferred aryl group.

The term "substituted aryl" refers to aryl groups substituted with one or more groups, preferably selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), and the like. The terms "cycloalkyl" and "cycloalkenyl" refer to mono-, bi-, or tri homocyclic ring groups of 3 to 15 carbon atoms which are, respectively, fully saturated and partially unsaturated. The term "cycloalkenyl" includes bi- and tricyclic ring systems that are not aromatic as a whole, but contain aromatic portions (e.g., fluorene, tetrahydronapthalene, dihydroindene, and the like). The rings of multi-ring cycloalkyl groups may be either fused, bridged and/or joined through one or more Spiro unions. The terms "substituted cycloalkyl" and "substituted cycloalkenyl" refer, respectively, to cycloalkyl and cycloalkenyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), and the like. The terms "carbocyclo", "carbocyclic" or "carbocyclic group" refer to both cycloalkyl and cycloalkenyl groups. The terms "substituted carbocyclo", "substituted carbocyclic" or "substituted carbocyclic group" refer to carbocyclo or carbocyclic groups substituted with one or more groups as described in the definition of cycloalkyl and cycloalkenyl.

The term "halogen" refers to fluorine, chlorine, bromine, and iodine.

The term "alkanoyl" refers to alkyl group (which may be optionally substituted as described above) linked to a carbonyl group (e.g., —C(O)-alkyl). Similarly, the term "aroyl" refers to an aryl group (which may be optionally substituted as described above) linked to a carbonyl group (e.g., —C(O)-aryl).

"Alkylamino" refers an alkyl group as defined above with the indicated number of carbon atoms attached through an amino bridge. An example of an alkylamino is methylamino, (i.e., —NH—CH3).

"Alkylsulfonyl" refers to an alkyl as defined above with the indicated number of carbon atoms attached through a sulfonyl bridge (i.e., —S(=O)2alkyl) such as mesyl and the like, and "Arylsulfonyl" refers to an aryl attached through a sulfonyl bridge (i.e., —S(=O)2aryl).

"Alkylsulfamoyl" refers to an alkyl as defined above with the indicated number of carbon atoms attached through a sulfamoyl bridge (i.e., —NHS(=O)2alkyl), and an "Arylsulfamoyl" refers to an alkyl attached through a sulfamoyl bridge (i.e., (i.e., —NHS(=O)2aryl).

"Alkylsulfinyl" refers to an alkyl as defined above with the indicated number of carbon atoms attached through a sulfinyl bridge (i.e. —S(=O)alkyl).

Non-aromatic mono or polycyclic alkyls are referred to herein as "carbocyclo" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

As used herein, "heterocyclo" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

"Alkylthio" refers to an alkyl group as defined above with the indicated number of carbon atoms attached through a sulfur bridge. An example of an alkylthio is methylthio, (i.e., —S—CH3).

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing a oxygen atom with a sulfur atom or replacing a amino group with a hydroxyl group. The derivative may be a prodrug. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O) ORb, —NRaSO2Rb, —C(=O)Ra, —C(=O)ORa, —C(=O)NRaRb, —OC(=O)NRaRb, —ORa, —SRa, —SORa, —S(=O)2Ra, —OS(=O)2Ra and —S(=O) 2ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, and heteroarylalkyl.

The term "optionally substituted," as used herein, means that substitution is optional and therefore it is possible for the designated atom to be unsubstituted.

Throughout the specification, groups and substituents thereof may be chosen to provide stable moieties and compounds.

To the extent that the disclosed compounds, and salts thereof, may exist in their tautomeric form, all such tautomeric forms are contemplated herein as part of the present disclosure.

All stereoisomers of the present compounds, such as those which may exist due to asymmetric carbons on the various substituents, including enantiomeric forms (which may exist even in the absence of asymmetric carbons) and diastereomeric forms, are contemplated within the scope of this disclosure. Individual stereoisomers of the compounds of the disclosure may, for example, be substantially free of other isomers, or may be admixed, for example, as racemates or with all other, or other selected, stereoisomers. The chiral centers of the compounds of the present disclosure can have the S or R configuration as defined by the IUPAC 1974 Recommendations.

The terms "including", "such as", "for example" and the like are intended to refer to exemplary embodiments and not to limit the scope of the present disclosure.

DETAILED DESCRIPTION

Aromatase is the enzyme complex responsible for the final step in estrogen synthesis, via the conversion of the androgens androstenedione and testosterone to the estrogens estrone ($E_1$) and estradiol ($E_2$), respectively. There are substantial data showing that estrogen promotes a number of cancers, including breast, endometrial, and ovarian [*Cochrane Database Syst. Rev.*, 7; (4): CD003370 (2009); Review. *Curr. Drug Targets.*, 11(4): 474-81 (2010); *Semin. Reprod. Med.*, 28(1): 81-90. (2010)]. Increasingly, these tissues have been recognized as important sites of estrogen production. For example, stromal cells in breast adipose tissue produce estrogen that is biologically active in both a paracrine and an autocrine manner. This is likely responsible for the observation that estrogen concentration in the healthy breasts of postmenopausal women is unexpectedly higher (four- to six-fold) than in serum and similar to those in premenopausal women. In addition up to 70% of breast cancer cells have been shown to synthesize estrogen as a result of intracellular aromatase expression [*Endocr. Rev.*, 24:152-82 (2003); *Endocr. Relat. Cancer*, 12: 701-20 (2005)]. There is increasing evidence that local estrogen production such as that in the breast may play a major role in the proliferation of ER+ tumors [*Breast Cancer*, 15: 270-277 (2008)]. Inhibiting estrogen at the source of its synthesis is therefore a logical target of ER+ cancer treatment.

The aromatase reaction is the final and limiting step in the estrogen biosynthesis pathway. As many ER+ cancer cells at least partly depend on estrogen stimulation, the first aromatase inhibitor that came into general clinical practice, aminoglutethimide, was successfully introduced for breast cancer treatment about three decades ago [*J. Clin. Oncol.*, 21: 984-90 (2003)]. However, due to its lack of specificity inhibiting several enzymes involved in adrenal steroid synthesis in addition to its aromatase inhibition and side effects, much effort has been spent on developing more selective, less toxic and more potent compounds. Thus, several "second-generation" drugs were developed. In general, these compounds had little effects on enzymes other than the aromatase in vivo; further, they revealed a better toxicity profile. However, similar to aminoglutethimide, they inhibited in vivo aromatization by 90% or less and did not improve clinical outcome when compared to tamoxifen or megestrol acetate as first- or second-line therapy, respectively, for metastatic breast cancer. In contrast, the "third generation" compounds, Anastrozole, Exemestane and Letrozole, all caused about 98% aromatase inhibition or better [*Expert Opin. Pharmacother.*, 10(9):1435-47 (2009)].

Although exemestane is highly effective in the inhibition of aromatase, its use has also been shown to result in potentially debilitating off target effects [*Cancer Treat. Rev.*, doi:10.1016/j.ctrv.2009.12.010 (2010)]. One of the most significant concerns that has been brought to light from clinical trials of exemestane is its potential effect on bone metabolism, as osteoporosis-related fractures are a major source of morbidity and mortality [*Drugs*, 69 (7): 889-918 (2009)]. Although it has been suggested that exemestane may have neutral or beneficial effects on bone density, the opposite has been shown in clinical trials; bone turnover rate is increased when compared to the second-generation ER+ treatment agent tamoxifen [*Lancet Oncol.*, 8 (2): 119-27 (2007); *Lancet*, 369 (9561): 559-70 (2007)].

Other exemestane-related side effects are just as serious and debilitating, and may possibly be unique to exemestane. For example, cognitive impairment is a concern in those subjected to ER+ cancer therapies, as estrogen deprivation has been found to have effects on cognition in women [*Cancer Treat. Rev.*, doi:10.1016/j.ctrv.2009.12.010 (2010)]. Unlike other third-generation aromatase inhibitors such as letrozol and the second-generation therapeutic agent tamoxifen, the use of exemestane increases cognition deficits, such as word finding [*Breast Cancer Res. Treat.*, 95(1): S97 (2005)]. Furthermore, other studies have demonstrated that exemestane use has been associated with additional side effects, such as severe hepatotoxicity, that are not observed with other aromatase inhibitors [*Breast Cancer Res. Treat.*, October 16. (Epub ahead of print) (2009)].

The pleiotropic effects of estrogens in its numerous target tissues, including the reproductive, skeletal, cardiovascular and central nervous systems are mediated in large part via ERs [*J. Steroid Biochem. Mol. Biol.*, 81: 225-230 (2001)], which are members of the super family of nuclear receptors and function as hormone-dependent transcription factors [*Endocrine Rev.*, 20: 358-417 (1999)]. ERs are capable of binding DNA directly through their central, conserved DNA-binding domains cognate DNA-binding motifs, also called estrogen response elements (EREs), have been characterized in estrogen-responsive promoters [*J. Cell Sci.*, 116:585-586 (2003); *Nucleic Acids Res.*, 12:8611-8626 (1984)]. Several different ERs are capable of interacting with estrogen and are responsible for mediating different aspects of transcriptional regulation [*J. Natl Canc. Inst.*, 93:2-4 (2001); *Proc. Natl Acad. Sci. USA.*, 99:15578-15583 (2002)].

In addition to mediating gene regulation through direct binding to DNA, ERs can regulate gene expression through protein-protein interaction with other transcription factors. This is also known as tethering. Several transcription factors were shown to mediate positive or negative transcriptional regulation by ERs in the absence of EREs, including AP1, Sp1, and NF-κB [*J. Steroid Biochem. Mol. Biol.*, 74: 311-317 (2000); *Vitam. Horm.*, 62: 231-252 (2001); *Trends Endo-* crinol. Metab., 16: 46-52 (2005)]. In addition, interference between estrogen signaling and other intracellular signaling pathways including the MAPK and PI3K pathways have been widely reported and may result from interactions between ERs and components of these signaling cascades [*EMBO J.*, 15:1292-1300 (1996)]. Finally, it has been suggested that estrogens may act also through a membrane receptor member of the GPCR family, GPR30 [*Mol. Endocrinol.*, 14:1649-1660 (2000)]. These so-called non-genomic mechanisms of action can lead to rapid kinase-mediated activation of transcription factors and thus modulate gene expression in response to estrogens.

Gene regulation by estrogen (i.e., genes regulated in the absence of de novo protein synthesis) can therefore result from at least three different mechanisms, including tethering and non-genomic action in addition to classical, ERE-mediated transcriptional regulation.

Compounds

Compounds, methods of their preparation and pharmaceutical compositions and methods of aromatase inhibition or treatment or prophylaxis of a hormone-related disorder including certain compounds of Formula A are provided

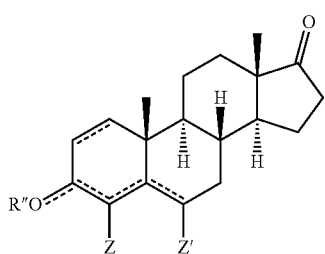

Formula A or pharmaceutically acceptable salts, ester, prodrugs or derivatives thereof, wherein

- - - - - represents a double bond either absent or present and R" is absent when the double bond is present or is H when the double bond is absent;

Z' is absent or is OR' and Z is absent or is OR, wherein when Z' is absent, Z is OR and when Z is absent Z' is OR';

R and R' are independently selected from H, a straight chained or branched $C_1$ to $C_8$ alkyl group, an alkenyl group, an alkynyl group, an alkanoyl group and an aroyl group, or substituted derivatives thereof. In certain embodiments, R and R' are independently selected from a substituted alkenyl or alkynyl group. The substituents can be any substituent known to one of ordinary skill, but in certain embodiments are selected from H, OH, phenyl, benzyl, naphthyl, substituted aryl, $C_1$ to $C_8$ alkyl group. Compounds of Formula A can comprise either two or three double bonds at the positions indicated.

In certain embodiments, methods of preparation of compounds of formula A are provided including: (i) substitution of a 1,4-diene-steroid or 4-ene-steroid; (ii) deconjugation to afforded a diazo-precursor; and (iii) reaction in the presence of either $Rh_2(S-DOSP)_4$ to afford a 4-substituted steroid, or AgOTf to furnish 6-a substituted steroid. In certain embodiments, the substitution is achieved through radical bromination of either a 1,4-diene-steroid or 4-ene-steroid. In certain subembodiments, the bromination is followed by debromination and deconjugation to afforded a diazo-precursor. In yet further embodiments, the steroid diazo resulting from step (ii) is reacted with an alcohol in the presence of either $Rh_2(S-DOSP)_4$ to afford a 4-substituted steroid, or AgOTf to furnish 6-a substituted steroid.

Further embodiments include the method of preparation of compounds of formula B. These methods include (i) substitution of a 1,4-diene-steroid or 4-ene-steroid; (ii) deconjugation to afforded a diazo-precursor; and (iii) reaction in the presence of either $Rh_2(S-DOSP)_4$ to afford a 4-substituted steroid. In certain embodiments, the substitution is achieved through radical bromination of either a 1,4-diene-steroid or 4-ene-steroid. In certain subembodiments, the bromination is followed by debromination and deconjugation to afforded a diazo-precursor. In yet further embodiments, the steroid diazo resulting from step (ii) is reacted with an alcohol in the presence of either $Rh_2(S-DOSP)_4$ to afford a 4-substituted steroid.

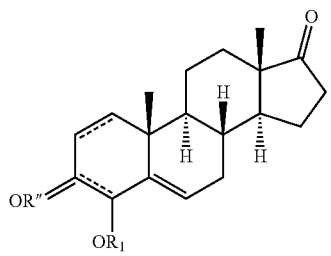

Formula B or pharmaceutically acceptable salts, ester, prodrugs or derivatives thereof, wherein (- - - - -) represents a double bond either absent or present and R" absent when the double bond is present and is H when the double bond is absent;

$R_1$ is selected from H, a straight chain or branched $C_1$ to $C_8$ alkyl group, an alkenyl group, an alkynyl group, an alkanoyl group and an aroyl group, any of which may be substituted. In certain embodiments, R1 is a substituted alkenyl or alkynyl group. In certain specific embodiments, R1 is a substituted group and the substituents are selected from OH, phenyl, benzyl, naphthyl, substituted aryl, $C_1$ to $C_8$ alkyl group. A further embodiment of the present disclosure includes the investigation of the three dimensional shape of the substrates, through the variation of the oxidation level at the $C_1$-$C_2$ bond of the substituted androstene dione steroid. Formula B can comprise either two or three double bonds.

Compounds, pharmaceutical compositions and methods of aromatase inhibition or treatment or prophylaxis of a hormone-related disorder including administering certain compounds of Formula B to a host in need thereof as described below are provided. Further aspects provide compounds, pharmaceutical compositions and methods of aromatase inhibition or treatment or prophylaxis of a hormone-related disorder including administering a compound of one of formula D, formula E, formula F and formula G, pharmaceutically acceptable salts, esters, prodrugs, or derivatives thereof.

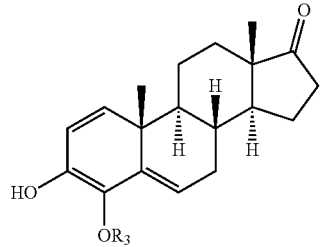

Formula D

Formula E

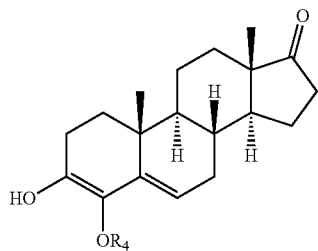

Formula F

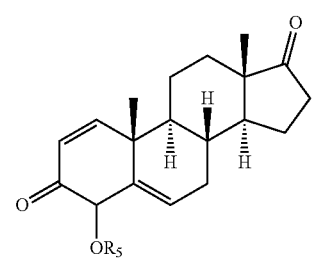

Formula G

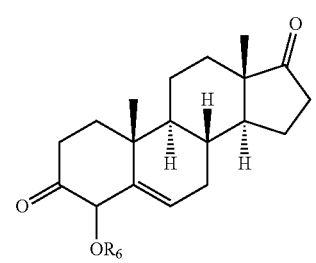

Wherein $R_3$, $R_4$, $R_5$ and $R_6$, are each independently selected from H, a straight chained or branched $C_1$ to $C_8$ alkyl group, an alkenyl group, an alkynyl group, an alkanoyl group and an aroyl group, any of which may be substituted. In certain embodiments, $R_3$, $R_4$, $R_5$ and $R_6$ are selected from a substituted alkenyl or alkynyl group. In certain specific embodiments, the substituents on the alkenyl and alkynyl group are OH, phenyl, benzyl, naphthyl, substituted aryl, $C_1$ to $C_8$ alkyl group.

$R_3$, $R_4$, $R_5$ and $R_6$ groups are typically selected from groups that enhance certain properties of the aromatase inhibitor including enhancing the solubility of the aromatase inhibitor, the ADME properties, the pharmacodynamics, the pharmacokinetics, diminish toxicity, augment bioavailability, or combinations thereof.

In other embodiments, $R_3$, $R_4$, $R_5$ and $R_6$, are each independently selected from a straight chained or branched $C_1$ to $C_8$ alkyl group, an alkenyl group, an alkynyl group; any of which may be substituted. Exemplary substituents of the alkenyl and alkynyl are OH, phenyl, benzyl, naphthyl, substituted aryl, and $C_1$ to $C_8$ alkyl groups.

In other embodiments, $R_3$, $R_4$, $R_5$ and $R_6$ are each independently selected from an alkenyl group, an alkynyl group, and a substituted alkenyl or alkynyl group, wherein the substituents are selected from OH, phenyl, benzyl, naphthyl, substituted aryl, $C_1$ to $C_8$ alkyl group.

In other embodiments, $R_3$, $R_4$, $R_5$ and $R_6$, are each independently selected from a substituted alkenyl or alkynyl group, wherein the substituents are selected from OH, phenyl, benzyl, naphthyl, substituted aryl, $C_1$ to $C_8$ alkyl group.

Another sub-embodiment provides compounds pharmaceutical compositions and methods of aromatase inhibition or treatment or prophylaxis of a hormone-related disorder including certain compounds of formula D, wherein on formula D, the group $R_3$ is chosen from an ethyl group, a benzyl group or a —$(CH_2)_n$C≡CH group, wherein the alkynyl chain and the aryl group may be either substituted or unsubstituted and n=0, 1, 2, 3, 5, 6 or 7.

Another sub-embodiment provides compounds pharmaceutical compositions and methods of aromatase inhibition or treatment or prophylaxis of a hormone-related disorder including certain compounds of formula E, wherein the group $R_4$ is a benzyl group or a substituted benzyl group and n=0, 1, 2, 3, 5, 6 or 7.

Another sub-embodiment provides compounds pharmaceutical compositions and methods of aromatase inhibition or treatment or prophylaxis of a hormone-related disorder including certain compounds of formula F, wherein $R_5$ is chosen from a methyl group, a tertiary butyl group, a —COBn group (wherein the aryl group may be substituted), a —$(CH_2)_n$ COEt group or a —$(CH_2)_n$C≡CH group, (wherein n=0, 1, 2, 3, 5, 6 or 7) and the alkenyl group may be either substituted or unsubstituted.

Another sub-embodiment provides compounds pharmaceutical compositions and methods of aromatase inhibition or treatment or prophylaxis of a hormone-related disorder including certain compounds of formula G, wherein $R_6$ is chosen from a methyl, ethyl or tertiary butyl group.

Formula D

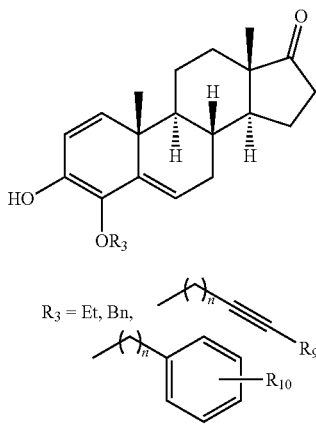

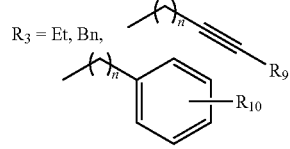

Formula E

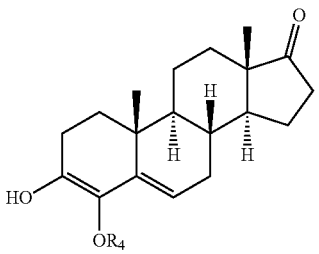

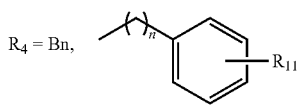

17

-continued

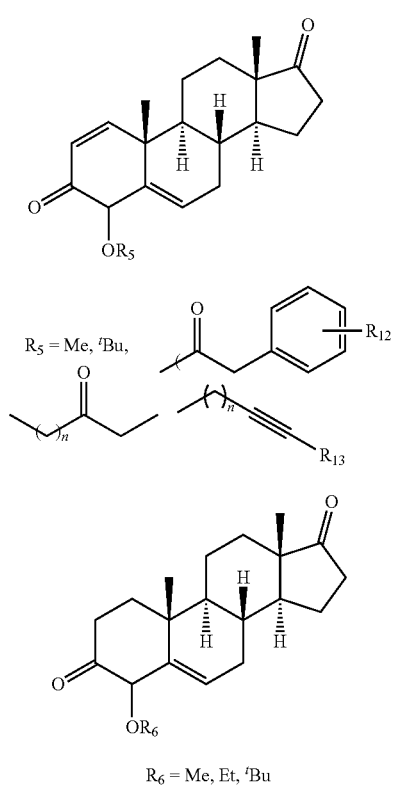

Formula F $R_5$ = Me, $^tBu$,

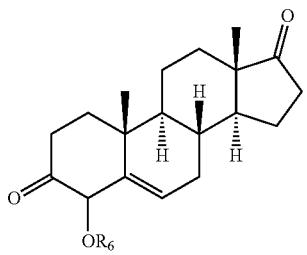

Formula G $R_6$ = Me, Et, $^tBu$

In certain embodiments, $R_9$, $R_{10}$, $R_{11}$, $R_{12}$ and $R_{13}$, are each independently selected from H, a straight chain or branched $C_1$ to $C_8$ alkyl group, a phenyl group, a benzyl group and an acyl group, any of which may be substituted or unsubstituted, a $(CH_2)_nOH$, wherein n=0, 1, 2, 3, 5, 6 or 7 and a halogen. In specific embodiments, $R_9$, $R_{10}$, $R_{11}$, $R_{12}$ and $R_{13}$, are independently selected from a substituted phenyl group, a substituted benzyl group, a naphthyl group, a substituted naphthyl group.

In other embodiments, $R_9$, $R_{10}$, $R_{11}$, $R_{12}$ and $R_{13}$, are each independently selected from a straight chain or branched $C_1$ to $C_8$ alkyl group, a substituted phenyl group, a substituted benzyl group, a substituted naphthyl group, a $(CH_2)_nOH$, wherein n=0, 1, 2, 3, 5, 6 or 7 and a halogen.

In another embodiment, $R_9$, $R_{10}$, $R_{11}$, $R_{12}$ and $R_{13}$ are each independently selected from an a $(CH_2)_nOH$, wherein n=0, 1, 2, 3, 5, 6 or 7, a substituted phenyl group and a substituted benzyl group.

In other embodiments of the present disclosure, the compounds, pharmaceutical compositions and methods of aromatase inhibition or treatment or prophylaxis of a hormone-related disorder including certain compounds disclosed herein, salts, prodrugs, or derivatives thereof are provided.

A separate embodiment of the present disclosure includes the method of preparation of compounds of formula C. These methods include (i) substitution of a 1,4-diene-steroid or 4-ene-steroid; (ii) deconjugation to afford a diazo-precursor; and (iii) reaction in the presence of AgOTf to afford a 6-substituted steroid. In certain embodiments, the substitution is achieved through radical bromination of either a 1,4-diene-steroid or 4-ene-steroid. In certain subembodiments, the bromination is followed by debromination and deconjugation to afforded a diazo-precursor. In yet further embodiments, the

18 steroid diazo resulting from step (ii) is reacted with an alcohol in the presence of AgOTf to afford a 6-substituted steroid.

FIG. 1

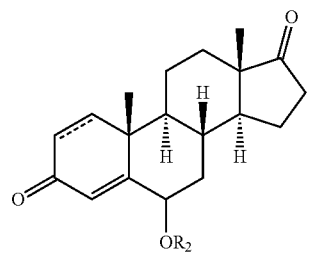

Formula C or pharmaceutically acceptable salts, ester, prodrugs or derivatives thereof, wherein

- - - - - represents a double bond either absent or present and R" absent when the double bond is present and is H when the double bond is absent;

$R_2$ is selected from H, a straight chain or branched $C_1$ to $C_8$ alkyl group, an alkenyl group, an alkynyl group, an alkanoyl group and an aroyl group, any of which may be substituted or unsubstituted. In certain embodiments, the substituents can be OH, phenyl, benzyl, naphthyl, substituted aryl, $C_1$ to $C_8$ alkyl group. In certain embodiments of Formula C, $R_2$ is a substituted alkenyl or alkynyl group. Formula C can comprise either two or three double bonds. One embodiment of the present disclosure includes the stereoselective control of the reactions, more specifically the preferential formation of the β-isomer. A further embodiment of the present disclosure includes the investigation of the three dimensional shape of the substrates, through the variation of the oxidation level at the $C_1$-$C_2$ bond of the substituted androstene dione steroid.

In certain embodiments, $R^2$ is alkyl, alkenyl or alkynyl optionally substituted with one or more, the same or different, $R^{21}$;

$R^{21}$ is alkyl, halogen, nitro, cyano, hydroxy, amino, mercapto, formyl, carboxy, carbamoyl, alkoxy, alkylthio, alkylamino, (alkyl)$_2$-amino, alkylsulfinyl, alkylsulfonyl, arylsulfonyl, carbocyclyl, aryl, or heterocyclyl, wherein $R^{21}$ is optionally substituted with one or more, the same or different, $R^{22}$; and $R^{22}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

Compounds, pharmaceutical compositions and methods of aromatase inhibition or treatment or prophylaxis of a hormone-related disorder including administering certain compounds of Formula C to a host in need thereof as described below are provided. Further aspects provide compounds, pharmaceutical compositions and methods of aromatase inhibition or treatment or prophylaxis of a hormone-related disorder including administering certain compounds of formula H and formula I, pharmaceutically acceptable salts, prodrugs, or derivatives thereof.

Formula H

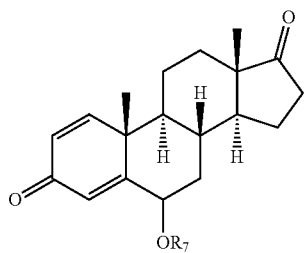

Formula I

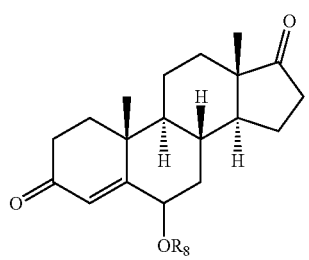

wherein

R_7 and R_8, are each independently selected from H, a straight chained or branched $C_1$ to $C_8$ alkyl group, an alkenyl group, an alkynyl group; an alkanoyl group and an aroyl group, any of which may be substituted or unsubstituted. In certain embodiments, the substituents on these groups are selected from H, OH, phenyl, benzyl, naphthyl, substituted aryl, $C_1$ to $C_8$ alkyl group. In specific embodiments, R_7 and R_8 are selected from a substituted alkenyl or alkynyl group. Generally, R_7 and R_8 substituents are selected from groups that enhance one or more properties of the aromatase inhibitor such as the solubility of the aromatase inhibitor, the ADME properties, the pharmacology, the pharmacodynamics, the pharmacokinetics, diminish toxicity, augment bioavailability, or combinations thereof.

In other embodiments, R_7 and R_8, are each independently selected from a straight chain or branched $C_1$ to $C_8$ alkyl group, an alkenyl group, an alkynyl group, any of which may be substituted, and typically the substituents are selected from OH, phenyl, benzyl, naphthyl, substituted aryl, $C_1$ to $C_8$ alkyl group.

In other embodiments, R_7 and R_8 are each independently selected from an alkenyl group, an alkynyl group, and a substituted alkenyl or alkynyl group, wherein the substituents are selected from OH, phenyl, benzyl, naphthyl, substituted aryl, $C_1$ to $C_8$ alkyl group.

In other embodiments, R_7 and R_8, are each independently selected from a substituted alkenyl or alkynyl group wherein the substituents are OH, phenyl, benzyl, naphthyl, substituted aryl, $C_1$ to $C_8$ alkyl group.

Another sub-embodiment provides compounds pharmaceutical compositions and methods of aromatase inhibition or treatment or prophylaxis of a hormone-related disorder including certain compounds of formula H pharmaceutically acceptable salts, prodrugs, or derivatives thereof, wherein R_7 is selected from a tertiary butyl group, a —COBn group, and a benzyl group, in all of which the aryl moiety may be substituted and n=0, 1, 2, 3, 5, 6 or 7; a substituted $C_{2-7}$ alkenyl group; a $(CH_2)_n OH$, wherein n=0, 1, 2, 3, 5, 6 or 7 and a substituted $C_{2-7}$ alkynyl group.

Another sub-embodiment provides compounds pharmaceutical compositions and methods of aromatase inhibition or treatment or prophylaxis of a hormone-related disorder including certain compounds of formula I, wherein R_8 is chosen from an alkenyl group or an alkynyl group, which may be substituted.

In all cases of compounds described herein, the "R" group comprising an alkene moiety includes both the cis and trans varieties.

Formula H

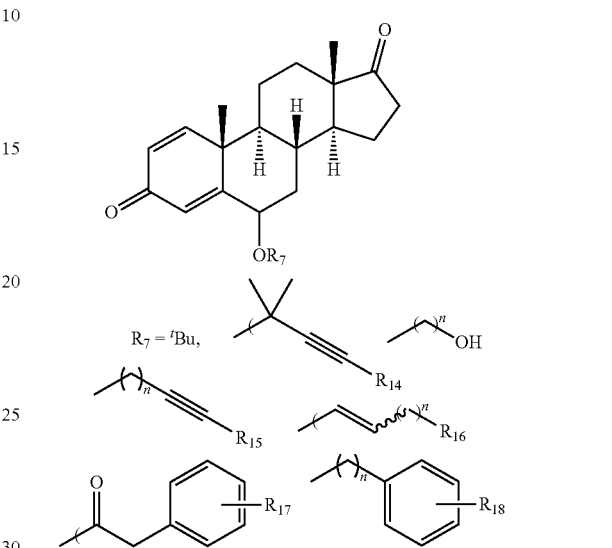

Formula I

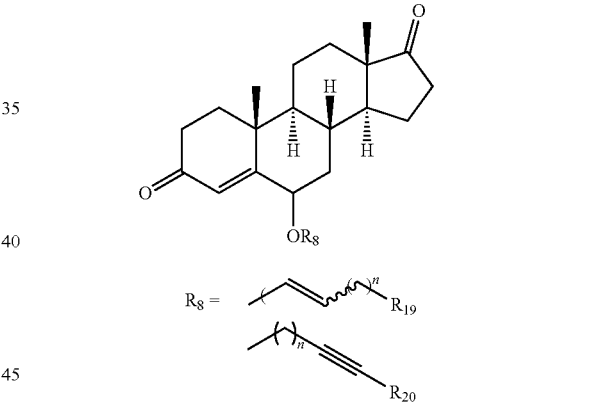

In certain embodiments, R_14, R_15, R_16, R_17, R_18 R_19 and R_20, are each independently selected from H, a straight chain or branched $C_1$ to $C_8$ alkyl group, a $(CH_2)_n OH$, wherein n=0, 1, 2, 3, 5, 6 or 7, a phenyl group, a $(CH_2)_n Ph$ group, wherein n=0, 1, 2, 3, 5, 6 or 7, a naphthyl group, an alkanoyl group and an aroyl group, any of which may be substituted, and a halogen.

In certain embodiments, R_14, R_15, R_16, R_17, R_18 R_19 and R_20, are each independently selected from H, a straight chain or branched $C_1$ to $C_8$ alkyl group, a $(CH_2)_n OH$, wherein n=0, 1, 2, 3, 5, 6 or 7, a phenyl group, a substituted phenyl group, a $(CH_2)_n Ph$ group, wherein n=0, 1, 2, 3, 5, 6 or 7 and the aryl ring may be substituted and alkanoyl group and an aroyl group.

In certain embodiments, R_14, R_15, R_16, R_17, R_18 R_19 and R_20, are each independently selected from H, a straight chain or branched $C_1$ to $C_8$ alkyl group, a $(CH_2)_n OH$, wherein n=0, 1, 2, 3, 5, 6 or 7, and a $(CH_2)_n Ph$ group, wherein n=0, 1, 2, 3, 5, 6 or 7 and the aryl ring may be substituted.

In other embodiments of the present disclosure, the use of compounds, pharmaceutical compositions and methods of aromatase inhibition or treatment or prophylaxis of a hormone-related disorder including certain compounds disclosed herein, pharmaceutically acceptable salts, prodrugs, or derivatives thereof are provided.

Methods of Use

The present disclosure provides methods of interfering, inhibiting, or blocking estrogen signal transduction through the estrogen biosynthetic pathway. Such inhibition can be accomplished by binding of aromatase or molecules associated with aromatase with the disclosed compounds or their derivatives to render aromatase inactive or unavailable. Alternatively, aromatase inhibition can also be achieved by interfering with the binding of aromatase or aromatase complexes to the aromatase substrates, including but not limited to, the androgens testosterone and androstenedione.

In certain embodiments, a method of treatment or prophylaxis of an estrogen-related disorder is provided comprising administering a compound described herein to a tissue that is estrogen-responsive. A tissue (for example, tumor) can be considered estrogen-responsive, which may mean, for example, the tissue contains elevated levels (rich) of an estrogen receptor. In one aspect, an estrogen-responsive disorder is characterized in a tissue that contains elevated levels of an estrogen receptor and cell proliferation (for example, tumor cell proliferation) is stimulated by circulating estrogen. Preferably, a tissue that contains elevated levels of an estrogen receptor can be considered as a "rich" tissue or receptor rich tissue. A rich tissue can be one that contains more (total percentage, ratio, count or the like) estrogen receptors than a tissue without an elevated level of the receptor. For example, a rich tissue can contain more than 90%, 80%, 70%, 60%, 50%, 40%, 30%, 20%, 10% of the total receptor count for a non-elevated tissue. Determining the level of receptors in a tissue is routine to those of ordinary skill in the art using conventional techniques. In one aspect, a tissue containing elevated levels of an estrogen receptor can be a tissue indicative or a disease state, for example, an estrogen-related disease state. For example, an estrogen receptor rich tissue can be a found in a patient suffering from an estrogen-related disorder. Exemplary estrogen-related disorders include osteoporosis, endometriosis, breast cancer, benign breast cancer, uterine cancer, ovarian cancer, polycystic ovarian disease, prostate cancer, benign prostatic hyperplasia (BPH), cardiac diseases, coronary artery disease, infertility, neurodegenerative disease, Alzheimer's disease, Parkinson's disease, or multiple sclerosis. In one aspect, osteoporosis, endometriosis, breast cancer, benign breast cancer, uterine cancer, ovarian cancer, polycystic ovarian disease, prostate cancer, benign prostatic hyperplasia (BPH), cardiac diseases, coronary artery disease, infertility, neurodegenerative disease, Alzheimer's disease, Parkinson's disease, or multiple sclerosis can be characterized by tissues in a patient that contain elevated levels of an estrogen receptor and/or and cell proliferation is stimulated by circulating estrogen.

One embodiment provides a method for the treatment or prevention of an estrogen-related pathology by administering to a host, for example a mammal, in need of such treatment, an aromatase inhibiting amount of disclosed compounds, compositions, derivatives, pharmaceutically acceptable salts, prodrugs, or combinations thereof.

Another embodiment provides a method of modulating aromatase activity in a cell, for example a eukaryotic cell, by contacting the cell with an aromatase inhibiting amount of the disclosed compounds, compositions, derivatives, pharmaceutically acceptable salts, prodrugs, or combinations thereof.

Still another embodiment provides a method of treating or preventing cancer or a tumor in a host by administering to the host an aromatase inhibiting amount of the disclosed compounds, compositions, derivatives, pharmaceutically acceptable salts, prodrugs, or combinations thereof.

Cancer is a general term for diseases in which abnormal cells divide without control. Cancer cells can invade nearby tissues and can spread through the bloodstream and lymphatic system to other parts of the body. It has been discovered that the administration of aromatase inhibitors to a host, for example a mammal, inhibits or reduces cancer, tumor growth or formation, and the metastasis of tumor cells.

There are several main types of cancer, and the disclosed compositions can be used to treat any type of cancer. For example, carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma is cancer that begins in the cells of the immune system.

When normal cells lose their ability to behave as a specified, controlled and coordinated unit, a tumor is formed. Generally, a solid tumor is an abnormal mass of tissue that usually does not contain cysts or liquid areas (some brain tumors do have cysts and central necrotic areas filled with liquid). A single tumor may even have different populations of cells within it with differing processes that have gone awry. Solid tumors may be benign (not cancerous), or malignant (cancerous). Different types of solid tumors are named for the type of cells that form them. Examples of solid tumors are sarcomas, carcinomas, and lymphomas. Leukemias (cancers of the blood) generally do not form solid tumors. The compositions described herein can be used to reduce, inhibit, or diminish the proliferation of tumor cells, and thereby assist in reducing the size of a tumor. In particular, the disclosed compositions are useful for the treatment of solid tumors or pathologies in instances of elevated estrogen production.

Representative cancers that may treated with the disclosed compositions and methods include, but are not limited to, bladder cancer, benign breast cancer, breast cancer, colorectal cancer, endometrial cancer, head & neck cancer, leukemia, lung cancer, lymphoma, melanoma, non-small-cell lung cancer, ovarian cancer, prostate cancer, testicular cancer, uterine cancer, cervical cancer, endometrial cancer, thyroid cancer, gastric cancer, brain stem glioma, cerebellar astrocytoma, cerebral astrocytoma, glioblastoma, ependymoma, Ewing's sarcoma family of tumors, germ cell tumor, extracranial cancer, Hodgkin's disease, leukemia, acute lymphoblastic leukemia, acute myeloid leukemia, liver cancer, medulloblastoma, neuroblastoma, brain tumors generally, non-Hodgkin's lymphoma, osteosarcoma, malignant fibrous histiocytoma of bone, retinoblastoma, rhabdomyosarcoma, soft tissue sarcomas generally, supratentorial primitive neuroectodermal and pineal tumors, visual pathway and hypothalamic glioma, Wilms' tumor, acute lymphocytic leukemia, adult acute myeloid leukemia, adult non-Hodgkin's lymphoma, chronic lymphocytic leukemia, chronic myeloid leukemia, esophageal cancer, hairy cell leukemia, kidney cancer, multiple myeloma, oral cancer, pancreatic cancer, primary central nervous system lymphoma, skin cancer, small-cell lung cancer, among others.

Accordingly, one embodiment provides a method of modulating gene transcription of estrogen target genes. This includes genes containing an ERE in the regulatory region of the gene, as well as genes whose transcription are regulated by estrogen tethering to other transcriptional regulators. Examples of ERE containing genes include, but are not limited to, Claudin-5, ligands of the Tgf-β signaling family, Lipocalin-2, Nuclear Receptor Interacting Protein-1, transcription elongation factor GreB, or ATP-binding cassette sub-family A member-3. Examples of estrogen target genes regulated by transcriptional tethering include, but are not limited to, those genes regulated by NF-κB, AP-1, or Sp1. Further examples of both types of estrogen target genes can be found in [*Nucleic Acids Res.*, 36(1): 76-93 (2008)]. A method of modulating gene expression in a cell, for example a tumor or cancer cell, is envisioned by contacting the cell with an aromatase inhibiting amount of one or more of the disclosed compounds, pharmaceutical salts, prodrugs, or derivatives thereof. Alternatively, such transcription can be inhibited in a host by administering to the host an aromatase inhibiting amount of the disclosed compounds and compositions.

Another embodiment provides a method of modulating gene expression in a tumor cell by contacting the tumor cell with an aromatase modulating amount of one or more of the disclosed compounds, compositions, pharmaceutically acceptable salts, derivatives or prodrugs thereof. The modulation of the estrogen biosynthetic pathway with the disclosed compounds and compositions can occur at transcriptional, translational and/or post-translational levels. The disclosed compounds can modulate gene transcription by binding to aromatase and preventing the synthesis of estrogen, thus preventing estrogen from forming complexes with other molecules including DNA and proteins. Alternatively, the disclosed compounds can bind aromatase and form aggresomes or other complexes that sequester aromatase or otherwise physically prevent aromatase from interacting with other biological molecules. Finally, the disclosed compounds and compositions can inhibit or interfere with the intracellular transport of aromatase including, but not limited to, the translocation of aromatase from the cytoplasm to the nucleus.

Adjuvant Therapy

Adjuvant therapy is a treatment given after the primary treatment to increase the chances of a cure. Adjuvant therapy may include chemotherapy, radiation therapy, hormone therapy, or biological therapy.

Because the principal purpose of adjuvant therapy is to kill any cancer cells that may have spread, treatment is usually systemic (uses substances that travel through the bloodstream, reaching and affecting cancer cells all over the body). Adjuvant therapy for breast cancer involves chemotherapy or hormone therapy, either alone or in combination. For example, research has shown that using chemotherapy as adjuvant therapy for early stage breast cancer helps to prevent the original cancer from returning. Adjuvant chemotherapy is usually a combination of anticancer drugs, which has been shown to be more effective than a single anticancer drug.

The strategy behind adjuvant hormone therapy is to deprive cancer cells of estrogen, which some breast cancer cells need to grow. Most often, adjuvant hormone therapy is treatment with the drug tamoxifen. However, for patients with early-stage, ER+ breast cancer have considerable residual risk for recurrence after completing 5 years of Tamoxifen adjuvant therapy [*J. Clin. Oncology*, 26(12): 1965-1971 (2008)]. Studies have demonstrated the efficacy of Exemestane as either additional or alternative adjuvant therapy [*Nat. Rev. Clin. Oncology*, 1: 24-25 (2004)].

It will be appreciated that the compounds of the present disclosure can also be administered as adjuvant therapies for the treatment of an estrogen-related pathology, for example cancer.

Neoadjuvant Therapy

Neoadjuvant therapy refers to a treatment given before the primary treatment. Examples of neoadjuvant therapy include chemotherapy, radiation therapy, and hormone therapy. For example, in treating breast cancer, neoadjuvant therapy allows patients with large breast cancer to undergo breast-conserving surgery.

It will be appreciated that the compounds of the present disclosure can also be administered as neoadjuvant therapies for the treatment of an estrogen-related pathology, for example cancer.

Pharmaceutical Compositions

Pharmaceutical compositions and dosage forms of the disclosure comprising a compound as described herein, or a pharmaceutically acceptable salt or prodrug thereof or a pharmaceutically acceptable polymorph, solvate, hydrate, dehydrate, co-crystal, anhydrous, or amorphous form thereof. Specific salts of disclosed compounds include, but are not limited to, sodium, lithium, potassium salts, and hydrates thereof.

Pharmaceutical compositions and unit dosage forms of the disclosure typically also comprise one or more pharmaceutically acceptable excipients or diluents. Advantages provided by specific compounds of the disclosure, such as, but not limited to, increased solubility and/or enhanced flow, purity, or stability (e.g., hygroscopicity) characteristics can make them better suited for pharmaceutical formulation and/or administration to patients than the prior art.

Pharmaceutical unit dosage forms of the compounds of this disclosure are suitable for oral, mucosal (e.g., nasal, sublingual, vaginal, buccal, or rectal), parenteral (e.g., intramuscular, subcutaneous, intravenous, intraarterial, or bolus injection), topical, or transdermal administration to a patient. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the compositions of the disclosure will typically vary depending on their use. For example, a dosage form used in the acute treatment of a disease or disorder may contain larger amounts of the active ingredient, for example the disclosed compounds or combinations thereof, than a dosage form used in the chronic treatment of the same disease or disorder. Similarly, a parenteral dosage form may contain smaller amounts of the active ingredient than an oral dosage form used to treat the same disease or disorder. These and other ways in which specific dosage forms encompassed by this disclosure will vary from one another will be readily apparent to those skilled in the art. See, e.g., Remington's Pharmaceutical Sciences, 18th ed., Mack Publishing, Easton, Pa. (1990).

Typical pharmaceutical compositions and dosage forms comprise one or more excipients. Suitable excipients are well known to those skilled in the art of pharmacy or pharmaceutics, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets or capsules may contain excipients not suited for use in parenteral dosage forms. The suitability of a particular excipient may also depend on the specific active ingredients in the dosage form. For example, the decomposition of some active ingredients can be accelerated by some excipients such as lactose, or when exposed to water. Active ingredients that comprise primary or secondary amines are particularly susceptible to such accelerated decomposition.

The disclosure further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers. In addition, pharmaceutical compositions or dosage forms of the disclosure may contain one or more solubility modulators, such as sodium chloride, sodium sulfate, sodium or potassium phosphate or organic acids. A specific solubility modulator is tartaric acid.

Like the amounts and types of excipients, the amounts and specific type of active ingredient in a dosage form may differ depending on factors such as, but not limited to, the route by which it is to be administered to patients. However, typical dosage forms of the compounds of the disclosure comprise a pharmaceutically acceptable salt, or a pharmaceutically acceptable polymorph, solvate, hydrate, dehydrate, co-crystal, anhydrous, or amorphous form thereof, in an amount of from about 10 mg to about 1000 mg, preferably in an amount of from about 25 mg to about 750 mg, and more preferably in an amount of from 50 mg to 500 mg.

Additionally, the compounds and/or compositions can be delivered using lipid- or polymer-based nanoparticles. For example, the nanoparticles can be designed to improve the pharmacological and therapeutic properties of drugs administered parenterally (Allen, T. M., Cullis, P. R. Drug delivery systems: entering the mainstream. Science. 303(5665):1818-22 (2004)).

Pharmaceutical compositions of the disclosure that are suitable for oral administration can be presented as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington's Pharmaceutical Sciences, 18th ed., Mack Publishing, Easton, Pa. (1990).

Typical oral dosage forms of the compositions of the disclosure are prepared by combining the pharmaceutically acceptable salt of disclosed compounds in an intimate admixture with at least one excipient according to conventional pharmaceutical compounding techniques. Excipients can take a wide variety of forms depending on the form of the composition desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, microcrystalline cellulose, kaolin, diluents, granulating agents, lubricants, binders, and disintegrating agents.

Due to their ease of administration, tablets and capsules represent the most advantageous solid oral dosage unit forms, in which case solid pharmaceutical excipients are used. If desired, tablets can be coated by standard aqueous or non-aqueous techniques. These dosage forms can be prepared by any of the methods of pharmacy. In general, pharmaceutical compositions and dosage forms are prepared by uniformly and intimately admixing the active ingredient(s) with liquid carriers, finely divided solid carriers, or both, and then shaping the product into the desired presentation if necessary.

For example, a tablet can be prepared by compression or molding. Compressed tablets can be prepared by compressing in a suitable machine the active ingredient(s) in a free-flowing form, such as a powder or granules, optionally mixed with one or more excipients. Molded tablets can be made by molding in a suitable machine a mixture of the powdered compound moistened with an inert liquid diluent.

Examples of excipients that can be used in oral dosage forms of the disclosure include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, and AVICEL-PH-105 (available from FMC Corporation, American Viscose Division, Avicel Sales, Marcus Hook, Pa., U.S.A.), and mixtures thereof. An exemplary suitable binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the disclosure is typically present in from about 50 to about 99 weight percent of the pharmaceutical composition or dosage form.

Disintegrants are used in the compositions of the disclosure to provide tablets that disintegrate when exposed to an aqueous environment. Tablets that contain too much disintegrant may swell, crack, or disintegrate in storage, while those that contain too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) should be used to form solid oral dosage forms of the disclosure. The amount of disintegrant used varies based upon the type of formulation and mode of administration, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used to form pharmaceutical compositions and dosage forms of the disclosure include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, clays, other algins, other celluloses, gums, and mixtures thereof.

Lubricants that can be used to form pharmaceutical compositions and dosage forms of the disclosure include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W. R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

This disclosure further encompasses lactose-free pharmaceutical compositions and dosage forms, wherein such compositions preferably contain little, if any, lactose or other mono- or di-saccharides. As used herein, the term "lactose-free" means that the amount of lactose present, if any, is insufficient to substantially increase the degradation rate of an active ingredient.

Lactose-free compositions of the disclosure can comprise excipients which are well known in the art and are listed in the USP (XXI)/NF (XVI), which is incorporated herein by reference. In general, lactose-free compositions comprise a pharmaceutically acceptable salt of an aromatase inhibitor, a binder/filler, and a lubricant in pharmaceutically compatible and pharmaceutically acceptable amounts. Preferred lactose-free dosage forms comprise a pharmaceutically acceptable salt of the disclosed compounds, microcrystalline cellulose, pre-gelatinized starch, and magnesium stearate.

This disclosure further encompasses anhydrous pharmaceutical compositions and dosage forms comprising the disclosed compounds as active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, Drug Stability: Principles & Practice, 379-80 (2nd ed., Marcel Dekker, NY, N.Y.: 1995). Water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the disclosure can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

Pharmaceutically acceptable salts of the disclosed compounds can be administered by controlled- or delayed-release means. Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Chemg-ju, Controlled Release Dosage Form Design, 2 (Technomic Publishing, Lancaster, Pa.: 2000).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under dosing a drug (i.e., going below the minimum therapeutic levels) as well as exceeding the toxicity level for the drug.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized; adsorbed salt forms of the disclosed compounds and thus effect controlled delivery of the drug. Examples of specific anion exchangers include, but are not limited to, Duolite® A568 and Duolite® AP143 (Rohm & Haas, Spring House, Pa. USA).

One embodiment of the disclosure encompasses a unit dosage form which comprises a pharmaceutically acceptable salt of the disclosed compounds (e.g., a sodium, potassium, or lithium salt), or a polymorph, solvate, hydrate, dehydrate, co-crystal, anhydrous, or amorphous form thereof, and one or more pharmaceutically acceptable excipients or diluents, wherein the pharmaceutical composition or dosage form is formulated for controlled-release. Specific dosage forms utilize an osmotic drug delivery system.

A particular and well-known osmotic drug delivery system is referred to as OROS® (Alza Corporation, Mountain View, Calif. USA). This technology can readily be adapted for the delivery of compounds and compositions of the disclosure. Various aspects of the technology are disclosed in U.S. Pat. Nos. 6,375,978 B1; 6,368,626 B1; 6,342,249 B1; 6,333,050 B2; 6,287,295 B1; 6,283,953 B1; 6,270,787 B1; 6,245,357 B1; and 6,132,420; each of which is incorporated herein by reference. Specific adaptations of OROS® that can be used to administer compounds and compositions of the disclosure include, but are not limited to, the OROS® Push-Pull™, Delayed Push-Pull™, Multi-Layer Push-Pull™, and Push-Stick™ Systems, all of which are well known. See, e.g. worldwide website alza.com. Additional OROS® systems that can be used for the controlled oral delivery of compounds and compositions of the disclosure include OROS®-CT and L-OROS®; see, Delivery Times, vol. 11, issue 11 (Alza Corporation).

Conventional OROS® oral dosage forms are made by compressing a drug powder (e.g., an aromatase inhibitor salt) into a hard tablet, coating the tablet with cellulose derivatives to form a semi-permeable membrane, and then drilling an orifice in the coating (e.g., with a laser). Kim, Chemg-ju, Controlled Release Dosage Form Design, 231-238 (Technomic Publishing, Lancaster, Pa.: 2000). The advantage of such dosage forms is that the delivery rate of the drug is not influenced by physiological or experimental conditions. Even a drug with a pH-dependent solubility can be delivered at a constant rate regardless of the pH of the delivery medium. But because these advantages are provided by a build-up of osmotic pressure within the dosage form after administration, conventional OROS® drug delivery systems cannot be used to effectively delivery drugs with low water solubility. Because aromatase inhibitor salts and complexes of this disclosure (e.g., an aromatase inhibitor sodium salt) may be far more soluble in water than an aromatase inhibitor itself, they may be well suited for osmotic-based delivery to patients. This disclosure does, however, encompass the incorporation of an aromatase inhibitor, and non-salt isomers and isomeric mixtures thereof, into OROS® dosage forms.

A specific dosage form of the compositions of the disclosure comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a dry or substantially dry state drug layer located within the cavity adjacent the exit orifice and in direct or indirect contacting relationship with the expandable layer; and a flow-promoting layer interposed between the inner surface of the wall and at least the external surface of the drug layer located within the cavity, wherein the drug layer comprises a salt of an aromatase inhibitor, or a polymorph, solvate, hydrate, dehydrate, co-crystal, anhydrous, or amorphous form thereof. See U.S. Pat. No. 6,368,626, the entirety of which is incorporated herein by reference.

Another specific dosage form of the disclosure comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being adapted to resist compaction forces sufficient to form a compacted drug layer without significant exudation of the liquid, active agent formulation, the dosage form optionally having a placebo layer between the exit orifice and the drug layer, wherein the active agent formulation comprises a salt of an aromatase inhibitor, or a polymorph, solvate, hydrate, dehydrate, co-crystal, anhydrous, or amorphous form thereof. See U.S. Pat. No. 6,342,249, the entirety of which is incorporated herein by reference.

Parenteral dosage forms can be administered to patients by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, administration DUROS®-type dosage forms, and dose-dumping.

Suitable vehicles that can be used to provide parenteral dosage forms of the disclosure are well known to those skilled in the art. Examples include, without limitation: sterile water; Water for Injection USP; saline solution; glucose solution; aqueous vehicles such as but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Compounds that alter or modify the solubility of a pharmaceutically acceptable salt of an aromatase inhibitor disclosed herein can also be incorporated into the parenteral dosage forms of the disclosure, including conventional and controlled-release parenteral dosage forms.

Topical dosage forms of the disclosure include, but are not limited to, creams, lotions, ointments, gels, shampoos, sprays, aerosols, solutions, emulsions, and other forms know to one of skill in the art. See, e.g., Remington's Pharmaceutical Sciences, 18th ed., Mack Publishing, Easton, Pa. (1990); and Introduction to Pharmaceutical Dosage Forms, 4th ed., Lea & Febiger, Philadelphia, Pa. (1985). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon), or in a squeeze bottle. Moisturizers or humectants can also be added to pharmaceutical compositions and dosage forms if desired. Examples of such additional ingredients are well known in the art. See, e.g., Remington's Pharmaceutical Sciences, 18.sup.th Ed., Mack Publishing, Easton, Pa. (1990).

Transdermal and mucosal dosage forms of the compositions of the disclosure include, but are not limited to, ophthalmic solutions, patches, sprays, aerosols, creams, lotions, suppositories, ointments, gels, solutions, emulsions, suspensions, or other forms known to one of skill in the art. See, e.g., Remington's Pharmaceutical Sciences, 18th Ed., Mack Publishing, Easton, Pa. (1990); and Introduction to Pharmaceutical Dosage Forms, 4th Ed., Lea & Febiger, Philadelphia, Pa. (1985). Dosage forms suitable for treating mucosal tissues within the oral cavity can be formulated as mouthwashes, as oral gels, or as buccal patches. Additional transdermal dosage forms include "reservoir type" or "matrix type" patches, which can be applied to the skin and worn for a specific period of time to permit the penetration of a desired amount of active ingredient.

Examples of transdermal dosage forms and methods of administration that can be used to administer the active ingredient(s) of the disclosure include, but are not limited to, those disclosed in U.S. Pat. Nos. 4,624,665; 4,655,767; 4,687,481; 4,797,284; 4,810,499; 4,834,978; 4,877,618; 4,880,633; 4,917,895; 4,927,687; 4,956,171; 5,035,894; 5,091,186; 5,163,899; 5,232,702; 5,234,690; 5,273,755; 5,273,756; 5,308,625; 5,356,632; 5,358,715; 5,372,579; 5,421,816; 5,466,465; 5,494,680; 5,505,958; 5,554,381; 5,560,922; 5,585,111; 5,656,285; 5,667,798; 5,698,217; 5,741,511; 5,747,783; 5,770,219; 5,814,599; 5,817,332; 5,833,647; 5,879,322; and 5,906,830, each of which are incorporated herein by reference in their entirety.

Suitable excipients (e.g., carriers and diluents) and other materials that can be used to provide transdermal and mucosal dosage forms encompassed by this disclosure are well known to those skilled in the pharmaceutical arts, and depend on the particular tissue or organ to which a given pharmaceutical composition or dosage form will be applied. With that fact in mind, typical excipients include, but are not limited to water, acetone, ethanol, ethylene glycol, propylene glycol, butane-1,3-diol, isopropyl myristate, isopropyl palmitate, mineral oil, and mixtures thereof, to form dosage forms that are non-toxic and pharmaceutically acceptable.

Depending on the specific tissue to be treated, additional components may be used prior to, in conjunction with, or subsequent to treatment with pharmaceutically acceptable salts of an aromatase inhibitor of the disclosure. For example, penetration enhancers can be used to assist in delivering the active ingredients to or across the tissue. Suitable penetration enhancers include, but are not limited to: acetone; various alcohols such as ethanol, oleyl, an tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as TWEEN 80 (polysorbate 80) and SPAN 60 (sorbitan monostearate).

The pH of a pharmaceutical composition or dosage form, or of the tissue to which the pharmaceutical composition or dosage form is applied, may also be adjusted to improve delivery of the active ingredient(s). Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of the active ingredient(s) so as to improve delivery. In this regard, stearates can serve as a lipid vehicle for the formulation, as an emulsifying agent or surfactant, and as a delivery-enhancing or penetration-enhancing agent. Different hydrates, dehydrates, co-crystals, solvates, polymorphs, anhydrous, or amorphous forms of the pharmaceutically acceptable salt of an aromatase inhibitor can be used to further adjust the properties of the resulting composition.

Combination Therapy

Another embodiment provides the combination of the compounds described herein and compositions with conventional chemotherapeutic agents and/or radiotherapy, either concurrently or simultaneously. For example, the disclosed compositions can be used to treat a pathology, for example a proliferative pathology such as cancer or other estrogen-related pathology independently or in combination with one another or with one or more additional therapeutic agents. Representative therapeutic agents include but are not limited to antibiotics, anti-inflammatories, anti-oxidants, analgesics, radioisotopes, chemotherapeutic agents such as nascopine, paclitaxel, nocodazole, vinca alkaloids, adriamycin, alkeran, anastrozole, Ara-C, BiCNU, busulfan, CCNU, carboplatinum, cisplatinum, cytoxan, daunorubicin, DTIC, 5-FU, fludarabine, hydrea, idarubicin, ifosfamide, letrozole, methotrexate, mithramycin, mitomycin, mitoxantrone, nitrogen, mustard, velban, vincristine, VP6, gemcitabine (gemzar), herceptin, irinotecan, (camptosar, CPT1), leustatin, navelbine, rituxan, STI-571, tamoxifen, taxotere, topotecan, (hycamtin), xeloda (capecitabine), zevelin, and combinations thereof.

In certain embodiments, a pharmaceutical composition comprising a compound as described herein and further comprising a second therapeutic agent is provided. In certain embodiments, the second therapeutic agent also inhibits aromatase activity. In certain specific embodiments, the second therapeutic agent is exemestane, letrozole, anastrozole, vorozole, formestane, fadrozole, tamoxifen, aminoglutethemide, testolactone, 4-hydroxyandrostenedione, 1,4,6-androstatrien-3,17-dione, 4-androstene-3,6,17-trione, or any combination thereof. In certain other embodiments, the second therapeutic agent is an antibody, antibiotic, anti-inflammatory, anti-oxidant, analgesic, radioisotope, noscapine, paclitaxel, nocodazole, vinca alkaloids, adriamycin, alkeran, Ara-C, BiCNU, busulfan, CCNU, carboplatinum, cisplatinum, Cytoxan, daunorubicin, DTIC, 5-FU, fludarabine, hydrea, idarubicin, ifosfamide, methotrexate, mithramycin, mitomycin, mitoxantrone, nitrogen, mustard, velban, vincristine, VP-16, gemcitabine, herceptin, irinotecan, camptosar, CPT-11, leustatin, navelbine, rituxan, STI-571, taxotere, temozolomide, topotecan, hycamtin, xeloda capecitabine, zevelin, and combinations thereof.

Kits

Typically, active ingredients of the pharmaceutical compositions of the disclosure are preferably not administered to a patient at the same time or by the same route of administration. This disclosure therefore encompasses kits which, when used by the medical practitioner, can simplify the administration of appropriate amounts of active ingredients to a patient.

A typical kit comprises a unit dosage form of a pharmaceutically acceptable salt of an aromatase inhibitor and optionally, a unit dosage form of a second pharmacologically active compound, such as anti-proliferative agent, or anticancer agent. In particular, the pharmaceutically acceptable salt of an aromatase inhibitor is the sodium, lithium, or potassium salt, or a polymorph, solvate, hydrate, dehydrate, co-crystal, anhydrous, or amorphous form thereof. A kit may further comprise a device that can be used to administer the active ingredient. Examples of such devices include, but are not limited to, syringes, drip bags, patches, and inhalers.

Kits of the disclosure can further comprise pharmaceutically acceptable vehicles that can be used to administer one or more active ingredients (e.g, an aromatase inhibitor). For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Other embodiments are directed to the use of the disclosed compositions in the preparation of a medicament for the treatment estrogen-related pathology.

EXAMPLES

The aromatase enzyme was co-crystallized with natural androgen substrates, by the methods according to [*Nature*, 457 (7226): 219-23 (2009)]. The crystal structure is disclosed in P.C.T. Patent Application US/2009/0204378, which is incorporated by reference in its entirety herein. The important interactions are highlighted in the cartoon of FIG. 1.

Surrounding positions 1 and 2 there are a number of hydrogen bonding interactions. There is a significant volume of free-space around the lower periphery of the substrate (between atoms 3-7), with hydrogen bonding around the 4-position interacting with the same amino acids associated with positions 1 and 2, and a hydrophobic pocket beside the 6-position, extending toward the access channel to the active site. Studies were focused around probing the steric and electronic functionalities that would be tolerated at the 4- and 6-positions.

The reactivity of the vinyl diazos was chosen as a platform upon which selective transformations could be performed. Initial assessment of reactivity was performed through a series of O—H insertions to provide substrates of interest for probing the enzyme active site. Preparation of these compounds was achieved using the three-step procedure illustrated below.

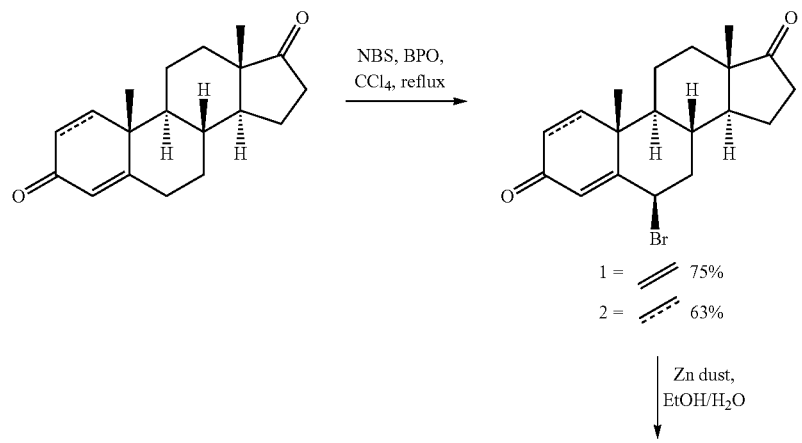

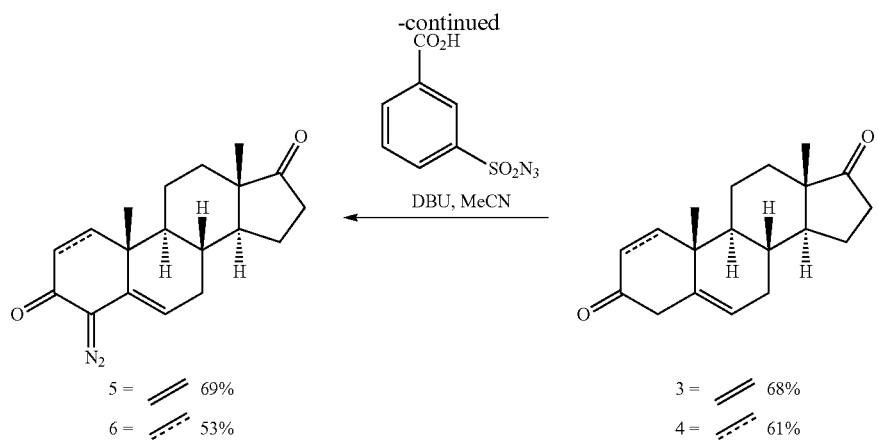

Radical bromination of both the 1,4-diene-steroid (to give 1 in Scheme I) and the 4-ene-steroid (to give 2 in Scheme I) proceeded in good yield. Debromination and deconjugation afforded the diazo-precursor (3 or 4) in good yield. Crystallization of the product and the diazo transfer step afforded good yield after purification. The diazo compounds were synthesized in batch wise bases to circumvent any deterioration.

Silver and Rh(II) catalyze O—H insertions with differential selectivity [*Nature*, 451: 417-424 (2008); *Tet. Let.* 48: 3975-3977 (2007)]. It was found that the reaction steroid diazos with $Rh_2(S\text{-DOSP})_4$ afforded primarily 4-substituted steroids, while the reaction catalyzed with AgOTf furnished 6-substituted steroids (Scheme II). This was true with both 1,4-diene-steroid diazo and 4-ene-steroid diazo compounds. Various alcohols were then used in the O—H insertion reactions with both catalysts to produce compound of Formula A.

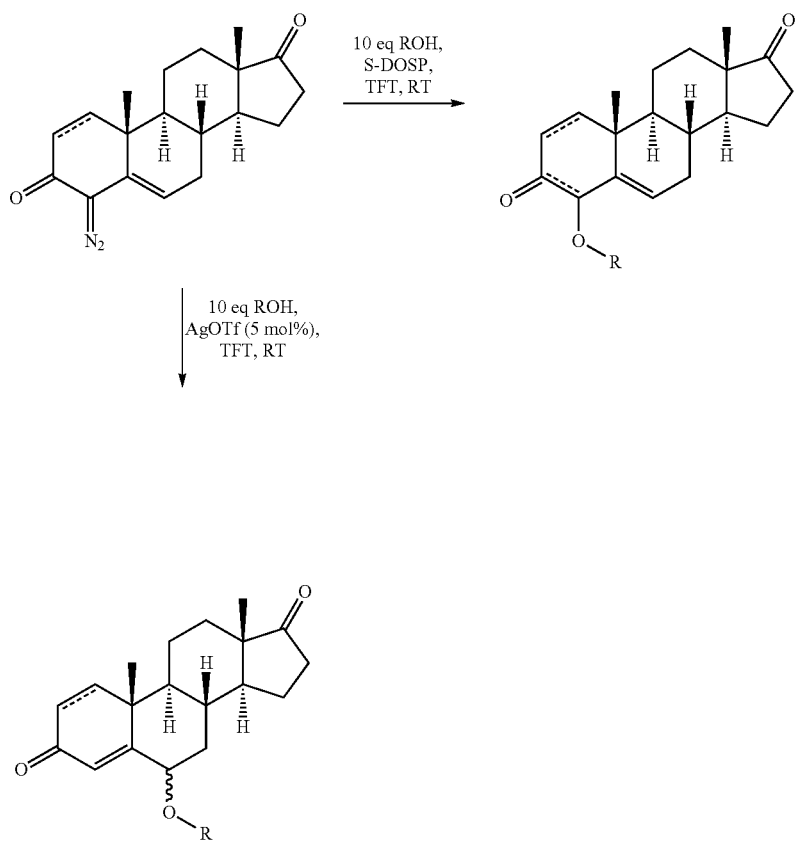

Scheme II

It was noted that a competing side reaction was a 1,4-hydride shift of the carbene. This shift afforded the stable triene 6, which, in general, could be separated from the desired product.

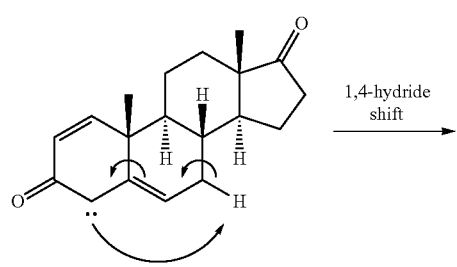

TABLE 1

Scope of the O—H insertion of the rhodium carbene.

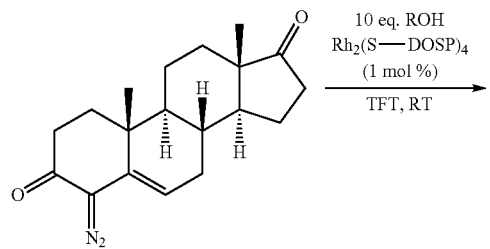

| entry | R | product | 4:6$^a$ | yield (%) |
|---|---|---|---|---|
| 1 | —CH$_2$CH$_3$ | 7a | 90:10 | 53 |
| 2 | —CH$_3$ | 7b | 93:7 | 44 |
| 3 | —CH$_2$Ph | 7c | >95:5 | 45 |
| 4 | —(CO)CH$_3$ | 7d | — | <5% |
| 5 | —(CO)CH$_2$Ph | 7e | — | <5% |

$^a$Ratio determined from the crude $^1$H-NMR

TABLE 2

Scope of the AgOTf mediated O—H Insertion of the carbene

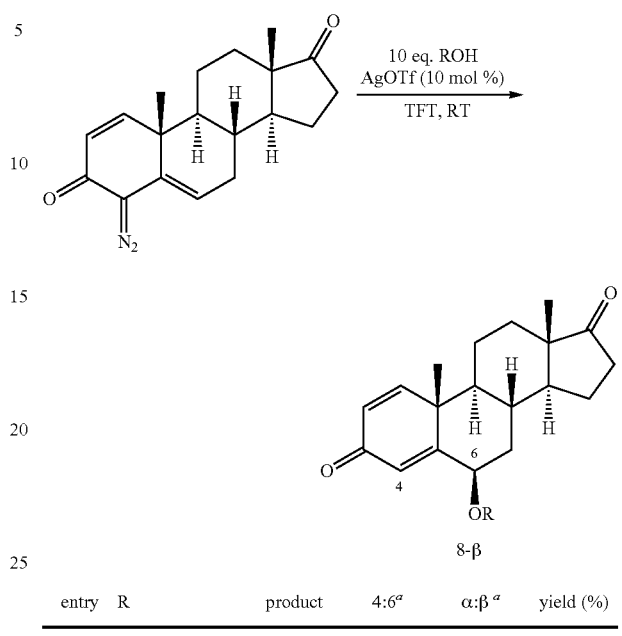

| entry | R | product | 4:6$^a$ | α:β$^a$ | yield (%) |
|---|---|---|---|---|---|
| 1 | —CH$_2$CH$_3$ | 8a | 10:90 | 15:85 | 41 |
| 2 | —CH$_3$ | 8b | 8:92 | 12:88 | 46 |
| 3 | —CH$_2$Ph | 8c | 5:>95 | 22:78 | 39 |
| 4 | —C(CH$_3$)$_3$ | 8d | 5:>95 | 8:92 | 70 |
| 5 | —(CO)CH$_3$ | 8e | 5:>95 | 5:>95 | 66 |
| 6 | —(CO)CH$_2$CH$_3$ | 8f | 5:>95 | 11:89 | 71 |
| 7 | —(CO)CH$_2$Ph | 8g | 5:>95 | 5:>95 | 38 |

$^a$Ratio determined from the crude $^1$H-NMR

TABLE 3

Scope of the O—H insertion of the silver carbene

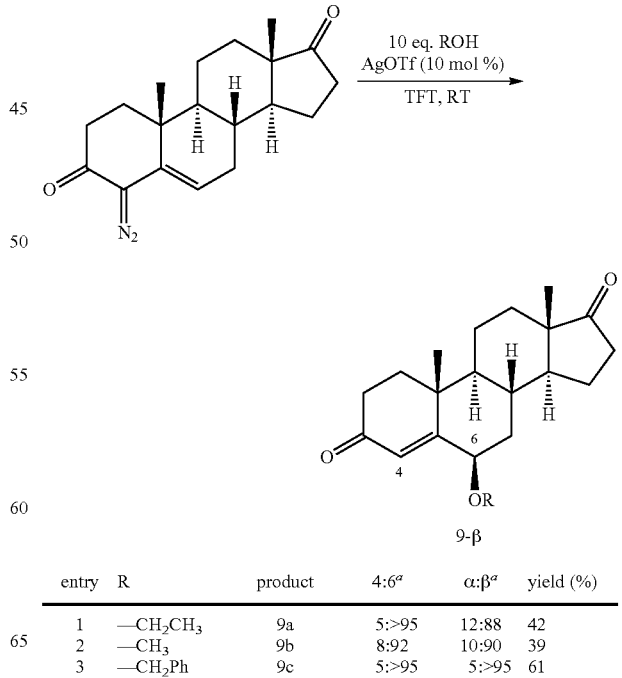

| entry | R | product | 4:6$^a$ | α:β$^a$ | yield (%) |
|---|---|---|---|---|---|
| 1 | —CH$_2$CH$_3$ | 9a | 5:>95 | 12:88 | 42 |
| 2 | —CH$_3$ | 9b | 8:92 | 10:90 | 39 |
| 3 | —CH$_2$Ph | 9c | 5:>95 | 5:>95 | 61 |

TABLE 3-continued

| 4 | —C(CH)$_3$ | 9d | 5:>95 | 5:>95 | 46 |
| 5 | —(CO)CH$_3$ | 9e | — | — | <5% |

[a] Ratio determined from the crude $^1$H-NMR

General Procedure for the O—H Insertion into Alcohols and Acids with Steroid Diazo Compounds An oven dried round-bottomed flask was charged with a solution of ROH (10 eq., 4.0 mmol), in degassed trifluorotoluene (5 mL), to which was added the catalyst (Rh$_2$(S-DOSP)$_4$: 1 mol %, 0.004 mmol; AgOTf: 5 mol %, 0.02 mmol), and the reaction stirred at room temperature for 10 minutes. A solution of steroid diazo (1 eq., 0.4 mmol), in degassed trifluorotoluene (3 mL), was added dropwise over 1 hr. The progress of the reaction was monitored by TLC, and upon consumption of the steroidal diazo starting material (between 2 and 16 hr), the reaction was concentrated under reduced pressure. Isolation was achieved using flash chromatography (eluting with Hexanes/EtOAc 80:20).

HDDG-044

(6R,8S,9S,10R,13S,14S)-6-butoxy-10,13-dimethyl-7,8,9,10,11,12,13,14,15,16-decahydro-3H-cyclopenta[α]phenanthrene-3,17(6H)-dione

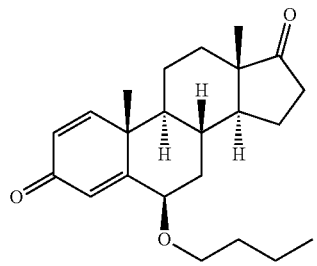

Isolated as a clear, colourless oil (26 mg; 68%); $^1$H NMR (400 MHz; CDCl$_3$) δ 7.01 (d, 1H, J=10.2 Hz, 1-CH), 6.19 (dd, J=10.2 and 1.9 Hz, 1H, 2-CH), 6.14 (d, J=1.9 Hz, 1H, 4-CH), 4.00 (t, J=3.2 Hz, 1H, 6-CH), 3.32 (dt, J=9.3 and 6.9 Hz, 1H, 20-CH$_A$), 3.23 (dt, J=9.3 and 6.9 Hz, 1H, 20-CH$_B$), 2.44 (dd, J=19.4 and 8.3 Hz, 1H, 16-CH$_A$), 2.20-2.10 (m, 2H), 2.05 (ddd, J=19.4, 9.8 and 8.1 Hz, 1H, 15-CHα), 1.97-1.77 (m, 3H), 1.76-1.54 (m, 2H), 1.54-1.46 (m, 2H), 1.35 (s, 3H, 19-CH$_3$), 1.35-1.19 (m, 5H), 1.06 (ddd, J=14.9, 10.2 and 4.2 Hz, 1H, 9-CH), 0.93 (s, 3H, 18-CH$_3$), 0.87 (t, J=7.4 Hz, 3H, 23-CH$_3$); $^{13}$C NMR (100 MHz, CDCl$_3$) δ 186.2, 163.8, 156.9, 127.8, 127.7, 127.1, 80.7, 69.0, 52.3, 50.9, 47.9, 43.8, 38.2, 35.9, 32.0, 31.4, 30.6, 22.1, 22.0, 19.6, 19.2, 14.2, 14.1; IR (film): 2953, 2869, 1736, 1662, 1624, 1090; m/z (APCI) 357.2 (100%, M+H), 283.2 (18%); HRMS-APCI m/z 357.2421 (C$_{23}$H$_{33}$O$_3$ requires 357.2424); [α]$^{20}$$_D$=+21.0 (c=0.2, CHCl$_3$); 92% pure by HPLC (Dynamax-60A; 3% i-PrOH/hexanes; R.T.=12.1 min).

HDDG-046

(6R,8S,9S,10R,13S,14S)-10,13-dimethyl-6-(pent-2-yn-1-yloxy)-7,8,9,10,11,12,13,14,15,16-decahydro-3H-cyclopenta[α]phenanthrene-3,17(6H)-dione

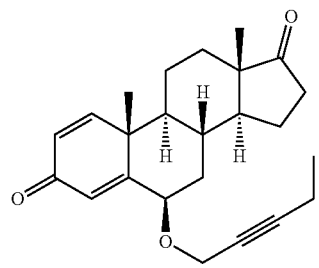

Isolated as a white solid (81 mg; 71%); $^1$H NMR (400 MHz; CDCl$_3$) δ 7.02 (d, 1H, J=9.8 Hz, 1-CH), 6.22 (s, 1H, 4-CH), 6.20 (dd, J=9.8 and 2.0 Hz, 1H, 2-CH), 4.30 (t, J=3.0 Hz, 1H, 6-CH), 4.11 (dt, J=15.3 and 3.0 Hz, 1H, 20-CH$_A$), 3.90 (dt, J=15.3 and 3.0 Hz, 1H, 20-CH$_B$), 2.44 (dd, J=19.3 and 8.5 Hz, 1H, 16-CHβ), 2.25-2.09 (m, 4H), 2.05 (dt, J=19.3 and 9.3 Hz, 1H, 16-CHα), 1.96-1.78 (m, 3H), 1.70 (ddd, J=13.5, 12.6 and 4.6 Hz, 1H, 8-CH), 1.60 (dt, J=9.2 and 3.3 Hz, 1H), 1.35 (s, 3H, 18-CH$_3$), 1.35-1.18 (m, 3H), 1.11 (t, J=7.4 Hz, 3H, 24-CH$_3$), 1.08 (dt, J=12.1 and 4.5 Hz, 1H, 9-CH), 0.92 (s, 3H, 19-CH$_3$); $^{13}$C NMR (100 MHz, CDCl$_3$) δ 186.1, 162.4, 156.9, 128.7, 127.2, 89.3, 78.6, 78.5, 74.7, 56.5, 52.1, 50.8, 47.9, 43.7, 38.0, 35.9, 31.4, 30.6, 22.1, 22.0, 19.3, 14.1, 14.0, 12.7; IR (film): 2939, 2245, 1736, 1662, 1453, 1052; m/z (APCI) 367.2 (100%, M+H), 283.2 (17%); HRMS-APCI m/z 367.2265 (C$_{24}$H$_{31}$O$_3$ requires 367.2268); [α]$^{20}$$_D$=+ 31.0 (c=0.25, CHCl$_3$); 91% pure by HPLC (Dynamax-60A; 3% i-PrOH/hexanes; R.T.=12.6 min).

HDDG-050

(8R,9S,10R,13S,14S)-4-(benzyloxy)-3-hydroxy-10,13-dimethyl-7,8,9,10,11,12,13,14,15,16-decahydro-1H-cyclopenta[α]phenanthren-17(2H)-one

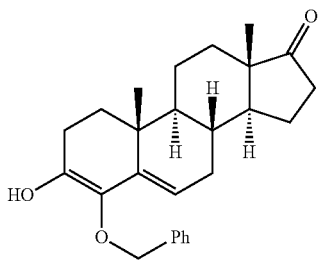

Isolated as a white solid (61 mg; 45%); $^1$H NMR (400 MHz; CDCl$_3$) δ 8.25 (br. s, 1H, O—H), 7.38-7.27 (m, 5H, Ar—H), 5.24 (t, J=3 Hz, 1H, 6-CH), 4.94 (d, J=11.1 Hz, 1H, 20-H$_A$), 4.83 (d, J=11.1 Hz, 1H, 20-H$_B$), 2.61 (ddd, J=17.1, 15.2 and 4.8 Hz, 1H, 2-Hα), 2.50-2.39 (m, 3H), 2.12-1.76 (m, 6H), 1.70-1.33 (m, 6H), 1.30 (s, 3H, 19-CH$_3$), 1.12 (ddd, J=11.3, 10.9 and 5.4 Hz, 1H, 9-CH), 0.85 (s, 3H, 18-CH$_3$); $^{13}$C NMR (100 MHz, CDCl$_3$) δ 195.5, 148.4, 147.3, 137.1, 130.3, 129.3, 128.6, 128.4, 76.7, 74.4, 54.1, 51.1, 47.7, 38.5, 36.4, 35.9, 34.7, 33.1, 31.4, 29.5, 21.8, 20.2, 18.5, 13.9; IR (film): 3454 (O—H), 2926, 2360, 1734, 1682, 1094; m/z (APCI) 391.2 (100%, M+H), 287.2 (16%); HRMS-APCI m/z 391.2263 (C$_{26}$H$_{31}$O$_3$ requires 391.2267); [α]$^{20}_D$=−12.0 (c=0.1, CHCl$_3$); 81% pure by HPLC (Dynamax-60A; 3% i-PrOH/hexanes; R.T.=8.6 min).

HDDG-053

(6R,8R,9S,10R,13S,14S)-6-((3-(3,4-dichlorophenyl)prop-2-yn-1-yl)oxy)-10,13-dimethyl-7,8,9,10,11,12,13,14,15,16-decahydro-3H-cyclopenta[α]phenanthrene-3,17(6H)-dione

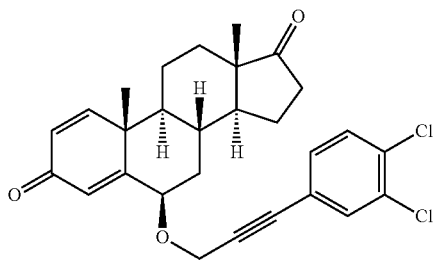

Isolated as a clear yellow oil (11 mg; 33%); $^1$H NMR (400 MHz; CDCl$_3$) δ 7.51 (d, 1H, J=1.9 Hz, Ar—H), 7.38 (d, J=8.3 Hz, 1H, Ar—H), 7.24 (dd, J=8.3 nd 1.9 Hz, 1H, Ar—H), 7.05 (d, J=10.1 Hz, 1H, 1-CH), 6.27 (d, J=1.9 Hz, 1H, 4-CH), 6.24 (dd, J=10.1 and 1.9 Hz, 1H, 2-CH), 4.36 (d, J=15.9 Hz, 1H, 20-CH$_A$), 4.35 (t, J=2.9 Hz, 1H, 6-CH), 4.15 (d, =15.9 Hz, 1H, 20-CH$_B$), 2.47 (dd, J=19.7 and 8.8 Hz, 1H, 16-CHα), 2.27 (dt, J=14.1 and 2.9 Hz, 1H), 2.23-2.03 (m, 2H), 1.99-1.81 (m, 3H), 1.73 (ddd, J=13.8, 12.5 and 4.8 Hz, 1H, 8-CH), 1.63 (ddd, J=10.2, 8.3 and 6.0 Hz, 1H), 1.40 (s, 3H, 19-CH$_3$), 1.38-1.20 (m, 3H), 1.13 (ddd, J=12.3, 4.4 and 3.6 Hz, 1H, 9-CH), 0.95 (s, 3H, 18-CH$_3$); $^{13}$C NMR (100 MHz, CDCl$_3$) δ 199.5, 186.0, 161.8, 156.8, 133.7, 131.1, 130.6, 128.9, 127.3, 122.4, 85.6, 84.7, 79.3, 56.5, 52.0, 50.8, 47.9, 43.7, 38.0, 35.9, 31.4, 30.6, 22.1, 22.0, 19.5, 14.1; IR (film): 2943, 1736, 1663, 1624, 1465, 1061; m/z (APCI) 483.1 (100%, M+H), 283.2 (33%); HRMS-APCI m/z 483.1486 (C$_{28}$H$_{29}$O$_3$Cl$_2$ requires 483.1488).

HDDG-054

(6R,8R,9S,10R,13S,14S)-10,13-dimethyl-6-((3-(naphthalen-1-yl)prop-2-yn-1-yl)oxy)-7,8,9,10,11,12,13,14,15,16-decahydro-3H-cyclopenta[α]phenanthrene-3,17(6H)-dione

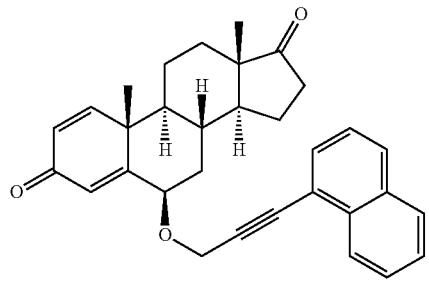

Isolated as a clear pale yellow oil (8 mg; 12%); $^1$H NMR (600 MHz; CDCl$_3$) δ 8.27 (d, 1H, J=8.1 Hz, Ar—H), 7.80 (br.d, J=10.2 Hz, 2H, Ar—H), 7.68 (d, J=7.2 Hz, 1H, Ar—H), 7.59-7.48 (m, 2H, Ar—H), 7.41 (t, J=8.1 Hz, 1H, Ar—H), 7.06 (d, J=10.2 Hz, 1H, 1-CH), 6.34 (d, J=1.8 Hz, 1H, 4-CH), 6.25 (dd, J=10.2 and 1.8 Hz, 1H, 2-CH), 4.53 (d, J=15.9 Hz, 1H, 20-CH$_A$), 4.49 (t, J=3 Hz, 1H, 6-CH), 4.33 (d, J=15.9 Hz, 1H, 20-CH$_B$), 2.47 (dd, J=19.6 and 9.0 Hz, 1H, 16-CHα), 2.31 (dt, J=14.6 and 3.5 Hz, 1H), 2.22 (ddd, J=12.0, 11.8 and 3.8 Hz, 1H), 2.08 (ddd, J=19.6, 9.4 and 8.6 Hz, 1H, 15-CHα), 2.00-1.82 (m, 3H), 1.75 (ddd, J=14.1, 13.6 and 5.5 Hz, 1H, 8-CH), 1.64 (ddd, J=12.7, 9.7 and 3.0 Hz, 1H, 11-CHα), 1.45 (s, 3H, 19-CH$_3$), 1.38 (ddd, J=14.2, 11.8 and 3.3 Hz, 1H, 9-CH), 1.32-1.09 (m, 3H), 0.96 (s, 3H, 18-CH$_3$); $^{13}$C NMR (100 MHz, CDCl$_3$) δ 186.0, 162.2, 156.8, 133.5, 133.3, 131.2, 129.4, 128.9, 128.6, 127.3, 127.2, 127.1, 126.7, 126.1, 125.4, 89.4, 85.1, 79.1, 56.9, 52.1, 50.8, 47.9, 43.8, 38.0, 35.9, 31.4, 30.6, 22.1, 22.0, 19.5, 14.1; IR (film): 2942, 1736, 1663, 1396, 1059; m/z (APCI) 465.2 (100%, M+H); HRMS-APCI m/z 465.2424 (C$_{32}$H$_{33}$O$_3$ requires 465.2424).

HDDG-055

(6R,8R,9S,10R,13S,14S)-6-(hex-2-yn-1-yloxy)-10,13-dimethyl-7,8,9,10,11,12,13,14,15,16-decahydro-1H-cyclopenta[α]phenanthrene-3,17(2H,6H)-dione

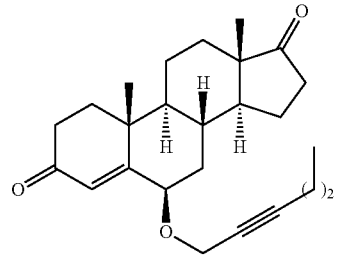

Isolated as a white solid (58 mg; 56%); $^1$H NMR (400 MHz; CDCl$_3$) δ 5.84 (s, 1H, 4-CH), 4.14 (t, J=3.4 Hz, 1H, 6-CH), 4.09 (dt, J=16.0 and 2.9 Hz, 1H, 20-H$_A$), 3.87 (dt, J=16.0 and 2.9 Hz, 1H, 20-CH$_B$), 2.55-2.34 (m, 3H), 2.19-2.00 (m, 7H), 1.95 (ddd, J=12.4, 8.4 and 5.8 Hz, 1H), 1.84 (dt, J=12.6 and 3.2 Hz, 1H), 1.69 (ddd, J=14.6, 13.8 and 4.6 Hz, 1H, 8-CH), 1.69-1.45 (m, 6H), 1.33-1.19 (m, 2H, 9-CH and 14-CH), 1.27 (s, 3H, 19-CH$_3$), 0.96 (t, J=7.3 Hz, 3H, 25-CH$_3$), 0.91 (s, 3H, 18-CH$_3$); $^{13}$C NMR (100 MHz, CDCl$_3$) δ 199.8, 163.2, 128.6, 87.7, 77.3, 77.2, 75.6, 55.7, 54.1, 51.3, 47.8, 38.4, 37.3, 36.8, 36.0, 34.4, 31.5, 30.2, 22.2, 21.9, 21.0, 20.4, 18.4, 14.0, 13.7; IR (film): 2937, 2871, 1731, 1681, 1454, 1052; m/z (APCI) 383.3 (100%, M+H), 365.3 (28%); HRMS-APCI m/z 383.2853 (C$_{25}$H$_{35}$O$_3$ requires 383.2851); [α]$^{20}_D$=+101.2 (c=1.0, CHCl$_3$); 88% pure by HPLC (Dynamax-60A; 3% i-PrOH/hexanes; R.T.=9.2 min).

HDDG-056

(6R,8R,9S,10R,13S,14S)-6-(hept-2-yn-1-yloxy)-10, 13-dimethyl-7,8,9,10,11,12,13,14,15,16-decahydro-1H-cyclopenta[α]phenanthrene-3,17(2H,6H)-dione

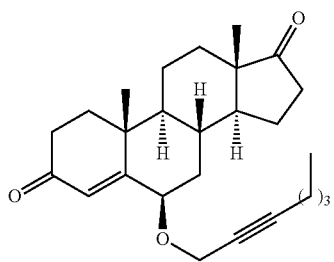

Isolated as a clear colourless oil (68 mg; 53%); $^1$H NMR (400 MHz; CDCl$_3$) δ 5.83 (s, 1H, 4-CH), 4.12 (t, J=2.9 Hz, 1H, 6-CH), 4.10 (dt, J=15.5 and 2.1 Hz, 1H, 20-H$_A$), 3.86 (dt, J=15.5 and 2.1 Hz, 1H, 20-H$_B$), 2.54-2.34 (m, 3H), 2.20-1.99 (m, 6H), 1.95 (ddd, J=12.3, 8.7 and 6.0 Hz, 1H), 1.84 (dt, J=13.2 and 3.4 Hz, 1H), 1.69 (ddd, J=14.8, 13.6 and 4.3 Hz, 1H, 8-CH), 1.67-1.53 (m, 2H), 1.40-1.28 (m, 6H), 1.28-1.18 (m, 2H), 1.27 (s, 3H, 19-CH$_3$), 0.96-0.89 (m, 1H, 9-CH), 0.90 (s, 3H, 18-CH$_3$), 0.88 (7.2, 3H, 26-CH$_3$); $^{13}$C NMR (100 MHz, CDCl$_3$) δ 199.9, 163.2, 128.6, 87.9, 77.3, 75.4, 55.7, 54.1, 51.3, 47.8, 38.4, 37.3, 36.8, 36.0, 34.4, 31.5, 30.9, 30.2, 22.2, 21.9, 20.4, 18.7, 18.4, 18.3, 14.0, 13.8; IR (film): 2935, 2859, 1737, 1681, 1228, 1052; m/z (APCI) 397.3 (100%, M+H), 285.2 (21%); HRMS-APCI m/z 397.2739 (C$_{26}$H$_{37}$O$_3$ requires 397.2737); [α]$^{20}_D$=+96.1 (c=1.0, CHCl$_3$); 95% pure by HPLC (Dynamax-60A; 3% i-PrOH/hexanes; R.T.=7.1 min).

HDDG-057

(6R,8R,9S,10R,13S,14S)-6-(dec-2-yn-1-yloxy)-10, 13-dimethyl-7,8,9,10,11,12,13,14,15,16-decahydro-1H-cyclopenta[α]phenanthrene-3,17(2H,6H)-dione

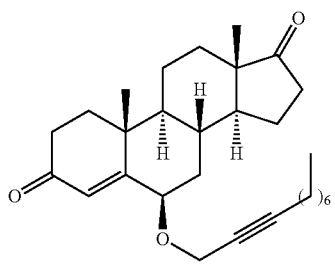

Isolated as a clear, colourless oil (38 mg; 58%); $^1$H NMR (400 MHz; CDCl$_3$) δ 5.83 (s, 1H, 4-CH), 4.12 (t, J=2.9 Hz, 1H, 6-CH), 4.10 (dt, J=15.4 and 2.1 Hz, 1H, 20-CH$_A$), 3.85 (dt, J=15.4 and 2.1 Hz, 1H, 20-CH$_B$), 2.55-2.33 (m, 3H, 16-CHα, 2-CH$_2$), 2.21-1.90 (m, 8H), 1.85 (dt, J=11.9 and 2.7 Hz, 1H), 1.75-1.53 (m, 4H), 1.52-1.40 (m, 3H), 1.37-1.19 (m, 9H), 1.26 (s, 3H, 19-CH$_3$), 0.97-0.91 (m, 1H, 9-CH), 0.89 (s, 3H, 18-CH$_3$), 0.85 (t, J=6.9 Hz, 3H, 29-CH$_3$); $^{13}$C NMR (100 MHz, CDCl$_3$) δ 199.8, 163.2, 128.6, 87.9, 77.3, 77.2, 75.4, 55.7, 54.1, 51.3, 47.8, 38.4, 37.3, 36.8, 35.8, 34.4, 31.9, 31.5, 30.2, 29.0, 28.9, 28.8, 22.8, 21.9, 20.4, 19.0, 19.4, 14.3, 14.0; IR (film): 2928, 2856, 1738, 1681, 1455, 1050; m/z (APCI) 439.3 (100%, M+H), 421.2 (11%); HRMS-APCI m/z 439.3206 (C$_2$H$_{43}$O$_3$ requires 439.3207); 84% pure by HPLC (Dynamax-60A; 3% i-PrOH/hexanes; R.T.=7.1 min).

HDDG-058

(6R,8R,9S,10R,13S,14S)-6-(cinnamyloxy)-10,13-dimethyl-7,8,9,10,11,12,13,14,15,16-decahydro-3H-cyclopenta[α]phenanthrene-3,17(6H)-dione

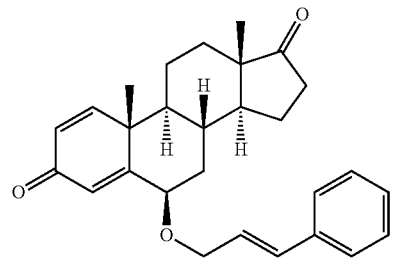

Isolated as a white solid (48 mg; 52%); $^1$H NMR (400 MHz; CDCl$_3$) δ 7.39-7.21 (m, 5H, Ar—H), 7.05 (d, J=10.2 Hz, 1H, 1-CH), 6.56 (d, J=15.9 Hz, 1H, 22-CH), 6.28-6.18 (m, 1H, 21-CH), 6.24 (dd, J=10.2 and 1.9 Hz, 1H, 2-CH), 6.20 (d, J=1.9 Hz, 1H, 4-CH), 4.15 (app. t, J=3.5 Hz, 1H, 6-CH), 4.11 (dd, J=11.4 and 7.9 Hz, 1H, 20-CH$_A$), 4.00 (dd, J=11.4 and 7.9 Hz, 1H, 20-CH$_B$), 2.46 (dd, J=19.4 and 8.5 Hz, 1H, 16-CHα), 2.26-1.99 (m, 3H), 1.98-1.81 (m, 2H), 1.80-1.53 (m, 3H), 1.42 (s, 3H, 19-CH$_3$), 1.38-1.18 (m, 3H), 1.11 (ddd, J=12.3, 7.8 and 3.8 Hz, 1H, 9-CH), 0.95 (s, 3H, 18-CH$_3$); $^{13}$C NMR (100 MHz, CDCl$_3$) δ 186.1, 163.1, 159.9, 136.6, 133.3, 128.8, 128.1, 126.7, 125.5, 79.6, 63.3, 52.3, 50.9, 47.9, 43.8, 38.2, 35.9, 31.4, 30.7, 22.1, 22.0, 19.4, 14.1; IR (film): 2941, 1736, 1663, 1451, 1053; m/z (APCI) 417.2 (100%, M+H), 283.2 (26%), 181.2 (35%); HRMS-APCI m/z 417.2424

($C_{28}H_{33}O_3$ requires 417.2424); 85% pure by HPLC (Dynamax-60A; 3% i-PrOH/hexanes; R.T.=14.8 min).

HDDG-059

(6R,8R,9S,10R,13S,14S)-10,13-dimethyl-6-(3-phenylpropoxy)-7,8,9,10,11,12,13,14,15,16-decahydro-3H-cyclopenta[α]phenanthrene-3,17(6H)-dione

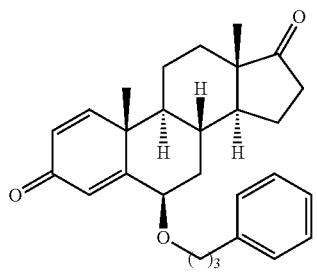

Isolated as a clear colourless oil (42 mg; 71%); $^1$H NMR (400 MHz; CDCl$_3$) δ 7.29-7.22 (m, 2H, Ar—H), 7.19-7.13 (m, 3H, Ar—H), 7.02 (d, J=10.2 Hz, 1H, 1-CH), 6.21 (dd, J=10.2 and 1.9 Hz, 1H, 2-CH), 6.14 (d, J=1.9 Hz, 1H, 4-CH), 3.98 (app. t, J=3.1 Hz, 1H, 6-CH), 3.39 (dt, J=9.2 and 6.4 Hz, 1H, 20-CH$_A$), 3.31-3.24 (m, 1H, 20-H$_B$), 2.71-2.61 (m, 2H, 22-CH$_2$), 2.47 (dd, J=19.5 and 8.4 Hz, 1H, 16-CHα), 2.22-2.00 (m, 4H), 2.00-1.79 (m, 3H), 1.77-1.57 (m, 3H), 1.36 (s, 3H, 19-CH$_3$), 1.33-1.19 (m, 3H), 1.12-1.04 (m, 1H, 9-CH), 0.95 (s, 3H, 18-CH$_3$); $^{13}$C NMR (100 MHz, CDCl$_3$) δ 186.2, 163.6, 156.9, 141.9, 128.6, 127.9, 127.2, 126.1, 80.9, 68.5, 52.2, 50.9, 47.9, 43.8, 38.1, 35.9, 32.6, 31.8, 31.4, 31.3, 30.6, 22.9, 22.1, 22.0, 19.2, 14.3, 14.2; IR (film): 2939, 2858, 1735, 1662, 1453, 1094; m/z (APCI) 419.3 (91%, M+H), 283.1 (100%); HRMS-APCI m/z 419.2581 ($C_2H_{35}O_3$ requires 419.2581).

HDDG-060

(6R,8R,9S,10R,13S,14S)-10,13-dimethyl-6-((5-phenylpentyl)oxy)-7,8,9,10,11,12,13,14,15,16-decahydro-3H-cyclopenta[α]phenanthrene-3,17(6H)-dione

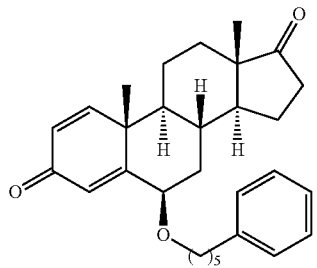

Isolated as a clear, colourless oil (32 mg; 49%); $^1$H NMR (400 MHz; CDCl$_3$) δ 7.27-7.22 (m, 2H, Ar—H), 7.17-7.12 (m, 3H, Ar—H), 7.01 (d, J=10.2 Hz, 1H, 1-CH), 6.21 (dd, J=10.2 and 2.1 Hz, 1H, 2-CH), 6.15 (d, J=2.1 Hz, 1H, 4-CH), 3.97 (app. t, J=3.4 Hz, 1H, 6-CH), 3.34 (ddd, J=13.8, 9.3 and 7.0 Hz, 1H, 20-CH$_A$), 3.23 (ddd, J=13.8, 9.0 and 6.8 Hz, 1H, 20-CH$_B$), 2.58 (t, J=7.9 Hz, 2H, 24-CH$_2$), 2.46 (dd, J=18.8 and 9.3 Hz, 1H, 16-CHα), 2.20-2.02 (m, 3H), 1.98-1.78 (m, 3H), 1.71 (ddd, J=17.6, 12.3 and 5.4 Hz, 1H, 8-CH), 1.67-1.53 (m, 6H), 1.35 (s, 3H, 19-CH$_3$), 1.34-1.17 (m, 4H), 1.12-1.04 (m, 1H, 9-CH), 0.94 (s, 3H, 18-CH$_3$); $^{13}$C NMR (100 MHz, CDCl$_3$) δ 186.2, 163.7, 156.9, 142.7, 128.6, 128.5, 127.9, 127.2, 125.9, 80.8, 69.2, 52.2, 50.9, 47.9, 43.8, 38.2, 36.0, 35.9, 31.5, 31.4, 30.6, 29.7, 26.1, 22.1, 22.0, 19.1, 14.1; IR (film): 2953, 2857, 1738, 1664, 1090; m/z (FTMS) 447.3 (100%, M+H), 303.1 (33%), 287.2 (25%); HRMS-APCI m/z 447.2895 ($C_{30}H_{39}O_3$ requires 447.2894); 92% pure by HPLC (Dynamax-60A; 3% i-PrOH/hexanes; R.T.=12.1 min).

HDDG-061

(6R,8R,9S,10R,13S,14S)-10,13-dimethyl-6-((E)-pent-2-en-1-yloxy)-7,8,9,10,11,12,13,14,15,16-decahydro-3H-cyclopenta[α]phenanthrene-3,17(6H)-dione

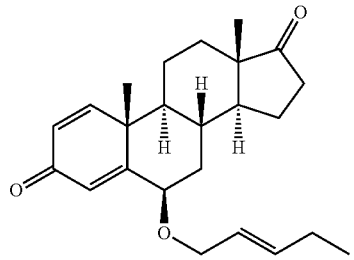

Isolated as a white solid (61 mg; 77%); $^1$H NMR (400 MHz; CDCl$_3$) δ 7.03 (d, 1H, J=10.2 Hz, 1-CH), 6.21 (dd, J=10.2 and 1.9 Hz, 1H, 2-CH), 6.15 (d, J=1.9 Hz, 1H, 4-CH), 5.70 (ddd, J=12.3, 8.5 and 5.7 Hz, 1H, 22-CH), 5.48 (ddd, J=11.9, 8.5 and 6.9 Hz, 1H, 21-CH), 4.08 (br. s, 1H, 6-CH), 3.90 (dd, J=11.9 and 5.7 Hz, 1H, 20-CH$_A$), 3.72 (dd, J=12.3 and 6.9 Hz, 1H, 20-CH$_B$), 2.46 (dd, J=19.6 and 9.1 Hz, 1H, 16-CHα), 2.24-1.98 (m, 3H), 1.98-1.80 (m, 3H), 1.75-1.45 (m, 4H), 1.38 (s, 3H, 19-CH$_3$), 1.35-1.13 (m, 3H), 1.08 (ddd, J=12.1, 10.0, 3.8 Hz, 1H, 9-CH), 0.98 (t, J=7.4 Hz, 3H, 24-CH$_3$), 0.94 (s, 3H, 18-CH$_3$); $^{13}$C NMR (100 MHz, CDCl$_3$) δ 186.2, 163.4, 157.0, 137.3, 128.2, 127.2, 124.7, 79.2, 69.5, 52.4, 50.9, 47.9, 43.8, 38.2, 35.9, 31.4, 30.6, 25.5, 22.1, 22.0, 19.2, 14.2, 13.5; IR (film): 2935, 1736, 1663, 1453, 1183, 1044; m/z (APCI) 369.2 (100%, M+H), 351.2 (32%), 283.2

(70%); HRMS-APCI m/z 369.2424 ($C_{24}H_{33}O_2$ requires 369.2424); 93% pure by HPLC (Dynamax-60A; 3% i-PrOH/hexanes; R.T.=11.6 min).

HDDG-062

(6R,8R,9S,10R,13S,14S)-10,13-dimethyl-6-((Z)-pent-2-en-1-yloxy)-7,8,9,10,11,12,13,14,15,16-decahydro-3H-cyclopenta[α]phenanthrene-3,17(6H)-dione

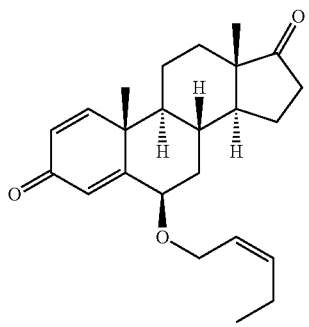

Isolated as a clear colourless oil (32 mg; 54%); $^1$H NMR (400 MHz; CDCl$_3$) δ 7.03 (d, 1H, J=10.1 Hz, 1-CH), 6.22 (dd, J=10.1 and 1.9 Hz, 1H, 2-CH), 6.18 (d, J=1.9 Hz, 1H, 4-CH), 5.61-5.53 (m, 1H, 22-CH), 5.49-5.42 (m, 1H, 21-CH), 4.07 (br. s, 1H, 6-CH), 3.95 (dd, J=11.8 and 5.8 Hz, 1H, 20-CH$_A$), 3.88 (dd, J=11.8 and 6.8 Hz, 1H, 20-H$_B$), 2.47 (dd, J=19.3 and 8.9 Hz, 1H, 16-Hα), 2.24-1.99 (m, 4H), 1.99-1.79 (m, 2H), 1.79-1.50 (m, 4H), 1.39 (s, 3H, 19-CH$_3$), 1.35-1.14 (m, 3H), 1.09 (ddd, J=12.3, 10.0 and 4.9 Hz, 1H, 9-CH), 0.95 (t, J=7.4 Hz, 3H, 24-CH$_3$), 0.94 (s, 3H, 18-CH$_3$); $^{13}$C NMR (100 MHz, CDCl$_3$) δ 186.2, 163.4, 157.0, 135.9, 128.1, 127.2, 125.0, 79.9, 64.5, 52.3, 50.9, 47.9, 43.8, 38.3, 35.9, 31.4, 30.6, 22.1, 22.0, 21.3, 19.2, 14.4, 14.1; IR (film): 2936, 1737, 1663, 1089; m/z (APCI) 369.2 (100%, M+H), 351.2 (37%), 283.2 (81%); HRMS-APCI m/z 369.2423 ($C_{24}H_{33}O_3$ requires 369.2424); 89% pure by HPLC (Dynamax-60A; 3% i-PrOH/hexanes; R.T.=11.3 min).

HDDG-063

(6R,8R,9S,10R,13S,14S)-10,13-dimethyl-6-(pentyloxy)-7,8,9,10,11,12,13,14,15,16-decahydro-3H-cyclopenta[α]phenanthrene-3,17(6H)-dione

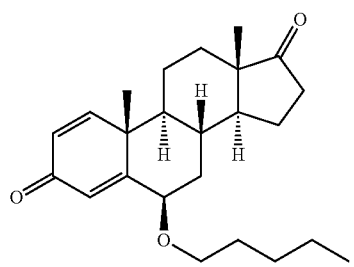

Isolated as a white solid (52 mg; 61%); $^1$H NMR (400 MHz; CDCl$_3$) δ 7.00 (d, 1H, J=10.2 Hz, 1-CH), 6.20 (dd, J=10.2 and 1.9 Hz, 1H, 2-CH), 6.14 (d, J=1.9 Hz, 1H, 4-CH), 3.97 (app. t, J=3.1 Hz, 1H, 6-CH), 3.36-3.28 (m, 1H, 20-CH$_A$), 3.25-3.19 (m, 1H, 20-CH$_B$), 2.46 (dd, J=19.1 and 8.9 Hz, 1H, 16-CHβ), 2.20-2.09 (m, 2H), 2.09-2.00 (m, 1H), 1.96-1.89 (m, 1H), 1.87-1.78 (m, 2H), 1.75-1.59 (m, 2H), 1.57-1.48 (m, 2H), 1.35 (s, 3H, 19-CH$_3$), 1.31-1.19 (m, 7H), 1.05 (dd, J=11.9 and 4.1 Hz, 1H, 9-CH), 0.93 (s, 3H, 18-CH$_3$), 0.86 (t, J=7.2 Hz, 3H, CH$_3$); $^{13}$C NMR (100 MHz, CDCl$_3$) δ 186.2, 163.8, 156.9, 127.8, 127.7, 80.7, 69.3, 52.3, 50.9, 47.9, 43.8, 38.2, 35.9, 31.4, 30.6, 29.5, 28.5, 22.7, 22.1, 22.0, 19.1, 14.2, 14.1; IR (film): 2958, 2874, 1739, 1664, 1454, 1091; m/z (APCI) 371 (100%, M+H), 283.2 (45%); HRMS-APCI m/z 371.2581 ($C_{24}H_{35}O_3$ requires 371.2581); 86% pure by HPLC (Dynamax-60A; 3% i-PrOH/hexanes; R.T.=10.2 min).

HDDG-066

(6R,8R,9S,10R,13S,14S)-6-(but-3-yn-1-yloxy)-10,13-dimethyl-7,8,9,10,11,12,13,14,15,16-decahydro-1H-cyclopenta[α]phenanthrene-3,17(2H,6H)-dione

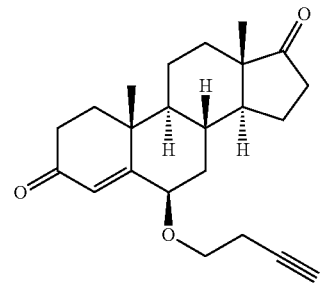

Isolated as a clear colourless oil (31 mg; 48%); $^1$H NMR (400 MHz; CDCl$_3$) δ 5.78 (s, 1H, 4-CH), 3.85 (t, J=2.9 Hz, 1H, 6-CH), 3.46 (ddd, J=14.1, 9.2 and 6.9 Hz, 1H, 20-CH$_A$), 3.32 (ddd, J=14.1, 9.6 and 7.8 Hz, 1H, 20-CH$_B$), 2.54-2.32 (m, 3H), 2.17-1.92 (m, 3H), 1.95 (t, J=2.7 Hz, 1H, 23-CH), 1.85 (app. dt, J=13.1 and 2.6 Hz, 1H), 1.75-1.58 (m, 3H), 1.53-1.39 (m, 4H), 1.29 (s, 4H, 19-CH$_3$), 1.29-1.20 (m, 3H), 0.98-0.92 (m, 1H), 0.92 (s, 3H, 18-CH$_3$); $^{13}$C NMR (100 MHz, CDCl$_3$) δ 199.8, 163.9, 128.2, 81.5, 80.2, 69.7, 66.5, 54.1, 51.3, 47.8, 38.3, 37.3, 36.9, 36.0, 35.4, 34.4, 31.5, 30.2, 21.9, 20.5, 19.9, 18.3, 14.1; IR (film): 2943, 2858, 1736, 1679, 1227, 1085; m/z (APCI) 355.2 (40%, M+H), 287.1 (85%), 285.2 (100%); HRMS-APCI m/z 355.2267 ($C_{23}H_{31}O_3$ requires 355.2268); 91% pure by HPLC (Dynamax-60A; 3% i-PrOH/hexanes; R.T.=8.8 min).

Measurement of Aromatase Activity by $^3$H-Water Method:

Purified P450arom (0.20 μg) was reconstituted with 2 μg P450-reductase (CPR) and 20 μg 1,2-diarachidoyl-sn-glycero-3-phosphocholine. Reconstituted P450arom was preincubated with 0.24 μM of the substrate, [1β-$^3$H, 4-$^{14}$C] androstenedione, with specific activity $2.7 \times 10^3$ dpm of $^3$H in 1 ml of 100 mM K-phosphate buffer at pH 7.4 containing 20% glycerol and 0.15% Emulgen913 (Em). Following preincubation at 37° C. for 10 minutes, the aromatase reaction was started by addition of 0.1 ml of 0.5 mM NADPH in 100 mM KPO4 buffer at pH 7.4 containing 20% glycerol. After shaking for 20 minutes at 37° C., the reaction was terminated by the addition of 0.4 ml of 20% trichloroacetic acid and 1.0 ml of 5% charcoal. After continued shaking at 37° C. for another 30 minutes, the mixture was centrifuged, and the supernatant is filtered through a cotton-plugged disposable Pasteur pipette. The $^3$H water in the eluate was assessed according to the 1β elimination mechanism (75% release into water). The specific activity of the purified P450arom was in the range 50-100 nmol/min/mg with Em as the detergent, one of the highest reported in the literature. The turnover number was calculated to be ~6/min. In the small molecule detergents β-D-nonyl maltopyranoside or 1 mM β-D-dodecyl maltopyranoside, the specific activity of P450arom is retained at 80-90% levels at 4° C. for weeks. The percent inhibition of compounds are provided for in the table below (compounds in FIGS. 2-7).

| Compound Number | yield % | % Inhibition Concentration (μmol) | | | | | | | | |
| --- | --- | --- | --- | --- | --- | --- | --- | --- | --- | --- |
| | | 10 | SD | SE | 1 | SD | SE | 0.1 | SD | SE |
| Letrazole | | 100 | | 0 | 98 | | 0 | 76 | | 0 |
| HDDG-001 | 64 | | | 0 | | | 0 | | | 0 |
| HDDG-002 | 75 | | | 0 | | | 0 | | | 0 |
| HDDG-003 | — | 80 | | 0 | 67 | | 0 | | | 0 |
| HDDG-004 | 67 | 40 | | 0 | 25 | | 0 | | | 0 |
| HDDG-005 | — | | | 0 | | | 0 | | | 0 |
| HDDG-006 | — | 84 | | 0 | 66 | | 0 | | | 0 |
| HDDG-007 | 61 | 0 | | 0 | 12 | | 0 | | | 0 |
| HDDG-008 | 62 | 0 | | 0 | 39 | | 0 | | | 0 |
| HDDG-009 | 46 | 55 | | 0 | | | 0 | | | 0 |
| HDDG-010 | 30 | 55 | | 0 | | | 0 | | | 0 |
| HDDG-011 | 49 | 37 | | 0 | | | 0 | | | 0 |
| HDDG-012 | 28 | 44 | | 0 | | | 0 | | | 0 |
| HDDG-013 | 21 | 48 | | 0 | | | 0 | | | 0 |
| HDDG-014 | 3 | 42 | | 0 | | | 0 | | | 0 |
| HDDG-015 | 70 | 54 | | 0 | | | 0 | | | 0 |
| HDDG-016 | 39 | 52 | | 0 | | | 0 | | | 0 |
| HDDG-017 | 62 | 64 | | 0 | | | 0 | | | 0 |
| HDDG-018 | 52 | 41 | | 0 | | | 0 | | | 0 |
| HDDG-019 | 41 | 54 | | 0 | | | 0 | 29 | | 0 |
| HDDG-020 | 44 | 61 | | 0 | 72 | | 0 | 21 | | 0 |
| HDDG-021 | 39 | 63 | | 0 | 70 | | 0 | 0 | | 0 |
| HDDG-022 | 55 | 86 | | 0 | 86 | | 0 | 51 | | 0 |
| HDDG-023 | 63 | 33 | | 0 | 30 | | 0 | 24 | | 0 |
| HDDG-024 | 46 | 76 | | 0 | 78 | | 0 | 16 | | 0 |
| HDDG-025 | 41 | 39 | 1.6 | 0.8 | 19 | 1.3 | 0.65 | | | 0 |
| HDDG-026 | 76 | 80 | 0.6 | 0.3 | 35 | 1.6 | 0.8 | 10 | 0.6 | 0.3 |
| HDDG-027 | 73 | 94 | 0.7 | 0.35 | 66 | 0.7 | 0.35 | 27 | 7.8 | 3.9 |
| HDDG-028 | 64 | 35 | 3.7 | 1.85 | 44 | 4.3 | 2.15 | 18 | 0.3 | 0.15 |
| HDDG-029 | 61 | 95 | 0.3 | 0.15 | 63 | 5.5 | 2.75 | 34 | 4.4 | 2.2 |
| HDDG-030 | 71 | 29 | 8.2 | 4.1 | 0 | 0 | 0 | 3 | 3.2 | 1.6 |
| HDDG-031 | 38 | 47 | 2.4 | 1.2 | 51 | 1.7 | 0.85 | 0 | 0 | 0 |
| HDDG-032 | 16 | 93 | 0.2 | 0.1 | 98 | 0.1 | 0.05 | 32 | 2.3 | 1.15 |
| HDDG-033 | 66 | 100 | 0.1 | 0.05 | 96 | 0.2 | 0.1 | 48 | 1.8 | 0.9 |
| HDDG-034 | 53 | 88 | 5.9 | 2.95 | 96 | 0.7 | 0.35 | 14 | 6 | 3 |
| HDDG-035 | 42 | | | | | | | | | |
| HDDG-036 | 2 | | | | | | | | | |
| HDDG-037 | 5 | | | | | | | | | |
| HDDG-038 | 71 | 91 | 0.4 | 0.2 | 97 | 0.5 | 0.25 | 22 | 12.5 | 6.25 |
| HDDG-039 | 68 | 88 | 2.2 | 1.1 | 98 | 0.4 | 0.2 | 33 | 7.3 | 3.65 |
| HDDG-040 | 21 | 98 | 0.2 | 0.1 | 94 | 0.5 | 0.25 | 54 | 2.1 | 1.05 |
| HDDG-041 | 61 | 87 | 0.4 | 0.2 | 95 | 0.3 | 0.15 | 34 | 4.4 | 2.2 |
| HDDG-042 | 48 | 99 | 0.1 | 0.05 | 95 | 0.8 | 0.4 | 40 | 4.7 | 2.35 |
| HDDG-043 | 52 | 90 | 1.8 | 0.9 | 97 | 0.3 | 0.15 | 18 | 2.7 | 1.35 |
| HDDG-044 | 68 | 86 | 1.3 | 0.65 | 96 | 0.4 | 0.2 | 73 | 1.2 | 0.6 |
| HDDG-045 | 64 | 95 | 0.4 | 0.2 | 94 | 0.3 | 0.15 | 47 | 2.4 | 1.2 |
| HDDG-046 | 71 | 99 | 0.1 | 0.05 | 96 | 0.4 | 0.2 | 89 | 0.6 | 0.3 |
| HDDG-047 | 62 | 99 | 0.1 | 0.05 | 95 | 0.3 | 0.15 | 42 | 10.9 | 5.45 |
| HDDG-048 | 53 | 97 | 0.1 | 0.05 | 87 | 0.6 | 0.3 | 48 | 3.4 | 1.7 |
| HDDG-049 | 50 | 75 | 1.6 | 0.8 | 87 | 1.1 | 0.55 | 5 | 7.4 | 3.7 |
| HDDG-050 | 45 | 100 | 0 | 0 | 96 | 0.3 | 0.15 | 75 | 2.6 | 1.3 |
| HDDG-051 | 42 | 90 | 0.8 | 0.4 | 94 | 0.7 | 0.35 | 40 | 2.3 | 1.15 |
| HDDG-052 | 54 | 87 | 0.8 | 0.4 | 95 | 0.3 | 0.15 | 47 | 2.8 | 1.4 |
| HDDG-053 | 33 | | | 0 | 91 | 0.5 | 0.25 | 95 | 0.1 | 0.05 |
| HDDG-054 | 12 | | | 0 | 92 | 0.6 | 0.3 | 94 | 0.9 | 0.45 |
| HDDG-055 | 56 | | | 0 | 84 | 0.8 | 0.4 | 77 | 0.7 | 0.35 |
| HDDG-056 | 53 | | | 0 | 86 | 2.1 | 1.05 | 80 | 1.1 | 0.55 |
| HDDG-057 | 58 | | | 0 | 92 | 0.3 | 0.15 | 94 | 0.3 | 0.15 |
| HDDG-058 | 52 | | | 0 | 94 | 0.5 | 0.25 | 95 | 0.6 | 0.3 |
| HDDG-059 | 71 | | | 0 | 94 | 0.4 | 0.2 | 97 | 0.3 | 0.15 |
| HDDG-060 | 49 | | | 0 | 96 | 0.5 | 0.25 | 97 | 0.1 | 0.05 |

-continued

| Compound Number | yield % | % Inhibition Concentration (μmol) | | | | | | | | |
|---|---|---|---|---|---|---|---|---|---|---|
| | | 10 | SD | SE | 1 | SD | SE | 0.1 | SD | SE |
| HDDG-061 | 77 | | | 0 | 93 | 0.4 | 0.2 | 96 | 0.3 | 0.15 |
| HDDG-062 | 54 | | | 0 | 96 | 0.3 | 0.15 | 97 | 0.4 | 0.2 |
| HDDG-063 | 61 | | | 0 | 97 | 0.1 | 0.05 | 96 | 0.5 | 0.25 |
| HDDG-064 | 32 | | | 0 | 96 | 0.4 | 0.2 | 96 | | 0 |
| HDDG-065 | 28 | | | 0 | 84 | 1.4 | 0.7 | 96 | 0.4 | 0.2 |

The invention claimed is:

1. A compound of Formula C, which is

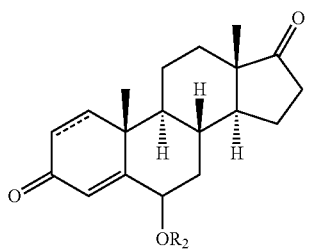

Formula C or a pharmaceutically acceptable salt thereof or a pharmaceutically acceptable ester thereof, wherein $R_2$ is selected from the group consisting of an alkenyl group and an alkynyl group, either of which may be optionally substituted.

2. A compound of claim 1, wherein the substituent is selected from OH, phenyl, benzyl, naphthyl, substituted aryl, or $C_1$ to $C_8$ alkyl group.

3. The compound of claim 1, wherein the substituent is selected from aryl, substituted aryl, heterocyclo, substituted heterocyclo, carbocyclo, substituted carbocyclo, or halo.

4. The compound of claim 1, wherein the substituent is selected from alkoxy, aryloxy, alkylester, arylester, alkanoyl or aryoyl, any of which may be optionally substituted.

5. The compound of claim 1, selected from the list:
(6R,8R,9S,10R,13S,14S)-10,13-dimethyl-6-((E)-pent-2-en-1-yloxy)-7,8,9,10,11,12,13,14,15,16-decahydro-3H-cyclopenta[a]phenanthrene-3,17(6H)-dione;
(6R,8R,9S,10R,13S,14S)-10,13-dimethyl-6-((Z)-pent-2-en-1-yloxy)-7,8,9,10,11,12,13,14,15,16-decahydro-3H-cyclopenta[a]phenanthrene-3,17(6H)-dione;
(6R,8R,9S,10R,13S,14S)-6-(cinnamyloxy)-10,13-dimethyl-7,8,9,10,11,12,13,14,15,16-decahydro-3H-cyclopenta[a]phenanthrene-3,17(6H)-dione;
(6R,8R,9S,10R,13S,14S)-10,13-dimethyl-6-(oct-2-yn-1-yloxy)-7,8,9,10,11,12,13,14,15,16-decahydro-3H-cyclopenta[a]phenanthrene-3,17(6H)-dione; and
(6R,8R,9S,10R,13S,14S)-10,13-dimethyl-6-(pent-2-yn-1-yloxy)-7,8,9,10,11,12,13,14,15,16-decahydro-3H-cyclopenta[a]phenanthrene-3,17(6H)-dione.

6. A pharmaceutical composition comprising a compound of claim 1 and a pharmaceutically acceptable excipient.

7. A method of treating a hormone-related disorder in a subject in need of such treatment comprising administering a pharmaceutical composition according to claim 6 to the subject.

8. The method of claim 7, wherein the subject is diagnosed with, or exhibiting symptoms of a hormone-related disorder.

9. The method of claim 7, wherein the hormone related disorder is osteoporosis, endometriosis, breast cancer, benign breast cancer, uterine cancer, ovarian cancer, polycystic ovarian disease, prostate cancer, or benign prostatic hyperplasia (BPH).

10. The method of claim 7, wherein the pharmaceutical composition is administered in combination with estrogen.

* * * * *